(12) United States Patent
Seidman et al.

(10) Patent No.: US 11,867,911 B2
(45) Date of Patent: *Jan. 9, 2024

(54) WEARABLE DEVICES AND WEARABLE ASSEMBLIES WITH ADJUSTABLE POSITIONING FOR USE IN AN OPTICAL MEASUREMENT SYSTEM

(71) Applicant: HI LLC, Los Angeles, CA (US)

(72) Inventors: Scott Jeremy Seidman, Glenview, IL (US); Jennifer Rines, Carlsbad, CA (US); Ryan Field, Culver City, CA (US); Isai Olvera, South Portland, ME (US); Zachary Phillip Sheldon, Venice, CA (US); Katherine Perdue, Los Angeles, CA (US)

(73) Assignee: HI LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/105,367

(22) Filed: Feb. 3, 2023

(65) Prior Publication Data

US 2023/0185096 A1 Jun. 15, 2023

Related U.S. Application Data

(63) Continuation of application No. 17/176,466, filed on Feb. 16, 2021, now Pat. No. 11,630,310.

(Continued)

(51) Int. Cl.
*G02B 27/01* (2006.01)
*G01S 17/04* (2020.01)
(Continued)

(52) U.S. Cl.
CPC ......... *G02B 27/0172* (2013.01); *G01S 17/04* (2020.01); *G01S 17/88* (2013.01); *G06F 1/163* (2013.01); *G06F 3/0304* (2013.01)

(58) Field of Classification Search
USPC ............................................................ 345/8
See application file for complete search history.

(56) References Cited

U.S. PATENT DOCUMENTS

| 4,321,930 A * | 3/1982 | Jobsis | A61B 5/0073 600/344 |
|---|---|---|---|
| 5,853,370 A | 12/1998 | Chance et al. | |

(Continued)

FOREIGN PATENT DOCUMENTS

| WO | 2011083563 | 7/2011 |
|---|---|---|
| WO | 2017083826 | 5/2017 |
| WO | 2018033751 | 2/2018 |

OTHER PUBLICATIONS

"International Search Report and Written Opinion dated Aug. 5, 2021 in International Application No. PCT/US2021/018189 with International Filing Date of Feb. 16, 2021".

(Continued)

*Primary Examiner* — Chineyere D Wills-Burns
(74) *Attorney, Agent, or Firm* — ALG Intellectual Property, LLC

(57) ABSTRACT

An optical measurement system includes a wearable device configured to be worn on a body of a user and a position alignment system. The wearable device includes a support assembly and a wearable assembly supported by the support assembly. The wearable assembly includes a plurality of light sources configured to emit a plurality of light pulses toward a target within the body of the user and a plurality of detectors each configured to receive a set of photons included in a light pulse included in the plurality of light pulses after the set of photons is scattered by the target. The position alignment system is configured to facilitate positioning of the wearable assembly at a same position on the body of the user during different use sessions of the wearable device.

20 Claims, 26 Drawing Sheets

Related U.S. Application Data

(60) Provisional application No. 63/086,350, filed on Oct. 1, 2020, provisional application No. 62/992,552, filed on Mar. 20, 2020, provisional application No. 62/979,866, filed on Feb. 21, 2020.

(51) Int. Cl.
*G01S 17/88* (2006.01)
*G06F 1/16* (2006.01)
*G06F 3/03* (2006.01)
*A61B 5/00* (2006.01)

(56) References Cited

U.S. PATENT DOCUMENTS

| | | | |
|---|---|---|---|
| 6,240,309 | B1 | 5/2001 | Yamashita et al. |
| 6,291,824 | B1 | 9/2001 | Battarbee et al. |
| 6,384,663 | B2 | 5/2002 | Cova et al. |
| 6,618,614 | B1 | 9/2003 | Chance |
| 6,640,133 | B2 | 10/2003 | Yamashita |
| 6,683,294 | B1 | 1/2004 | Herbert et al. |
| 7,356,365 | B2 | 4/2008 | Schurman |
| 7,547,872 | B2 | 6/2009 | Niclass et al. |
| 7,774,047 | B2 | 8/2010 | Yamashita et al. |
| 8,026,471 | B2 | 9/2011 | Itzler |
| 8,078,250 | B2 | 12/2011 | Chen et al. |
| 8,082,015 | B2 | 12/2011 | Yodh et al. |
| 8,633,431 | B2 | 1/2014 | Kim |
| 8,817,257 | B2 | 8/2014 | Herve |
| 9,058,081 | B2 | 6/2015 | Baxter |
| 9,076,707 | B2 | 7/2015 | Harmon |
| 9,131,861 | B2 | 9/2015 | Ince et al. |
| 9,316,735 | B2 | 4/2016 | Baxter |
| 9,401,448 | B2 | 7/2016 | Bienfang et al. |
| 9,419,635 | B2 | 8/2016 | Kumar et al. |
| 9,442,201 | B2 | 9/2016 | Schmand et al. |
| 9,529,079 | B1 | 12/2016 | Droz |
| 9,574,936 | B2 | 2/2017 | Heinonen |
| 9,946,344 | B2 | 4/2018 | Ayaz et al. |
| D817,553 | S | 5/2018 | Aaskov et al. |
| D825,112 | S | 8/2018 | Saez |
| 10,158,038 | B1 | 12/2018 | Do Valle et al. |
| 10,340,408 | B1* | 7/2019 | Katnani ......... H01L 31/022408 |
| 10,424,683 | B1 | 9/2019 | Do Valle |
| 10,515,993 | B2 | 12/2019 | Field et al. |
| 10,541,660 | B2 | 1/2020 | McKisson |
| 10,695,167 | B2 | 6/2020 | Van Heugten et al. |
| 10,697,829 | B2 | 6/2020 | Delic |
| 10,772,561 | B2 | 9/2020 | Donaldson |
| 10,809,796 | B2 | 10/2020 | Armstrong-Muntner |
| 10,912,504 | B2 | 2/2021 | Nakaji |
| 11,006,876 | B2 | 5/2021 | Johnson |
| 11,006,878 | B2 | 5/2021 | Johnson |
| 11,137,283 | B2 | 10/2021 | Balamurugan et al. |
| 11,630,310 | B2* | 4/2023 | Seidman ............. A61B 5/0075 345/8 |
| 2006/0264722 | A1 | 11/2006 | Hannula et al. |
| 2007/0083097 | A1 | 4/2007 | Fujiwara |
| 2009/0012402 | A1 | 1/2009 | Mintz |
| 2010/0188649 | A1 | 7/2010 | Prahl et al. |
| 2010/0249557 | A1 | 9/2010 | Besko et al. |
| 2011/0208675 | A1 | 8/2011 | Shoureshi et al. |
| 2012/0083673 | A1* | 4/2012 | Al-Ali ................. A61B 5/6814 600/301 |
| 2013/0342835 | A1 | 12/2013 | Blacksberg |
| 2014/0191115 | A1 | 7/2014 | Webster et al. |
| 2014/0217264 | A1 | 8/2014 | Shepard |
| 2014/0275891 | A1 | 9/2014 | Muehlemann et al. |
| 2015/0038811 | A1 | 2/2015 | Asaka |
| 2015/0038812 | A1* | 2/2015 | Ayaz ................. A61B 5/14553 600/328 |
| 2015/0041625 | A1 | 2/2015 | Dutton |
| 2015/0054111 | A1 | 2/2015 | Niclass et al. |
| 2015/0077279 | A1 | 3/2015 | Song |
| 2015/0150505 | A1 | 6/2015 | Kaskoun et al. |
| 2015/0157262 | A1* | 6/2015 | Schuessler .......... A61B 5/0533 600/479 |
| 2015/0157435 | A1* | 6/2015 | Chasins ................ A61D 13/00 600/549 |
| 2015/0201841 | A1 | 7/2015 | Ishikawa et al. |
| 2015/0327777 | A1 | 11/2015 | Kostic et al. |
| 2015/0364635 | A1 | 12/2015 | Bodlovic et al. |
| 2017/0030769 | A1 | 2/2017 | Clemens et al. |
| 2017/0052065 | A1 | 2/2017 | Sharma et al. |
| 2017/0176596 | A1 | 6/2017 | Shpunt et al. |
| 2017/0179173 | A1 | 6/2017 | Mandai et al. |
| 2017/0202518 | A1 | 7/2017 | Furman et al. |
| 2017/0281086 | A1 | 10/2017 | Donaldson |
| 2017/0363467 | A1 | 12/2017 | Clemens et al. |
| 2017/0367650 | A1* | 12/2017 | Wallois ................... G06F 3/015 |
| 2018/0014741 | A1 | 1/2018 | Chou |
| 2018/0020960 | A1* | 1/2018 | Sarussi ............. G01N 33/4925 600/310 |
| 2018/0027196 | A1 | 1/2018 | Yang et al. |
| 2018/0039053 | A1 | 2/2018 | Kremer et al. |
| 2018/0070830 | A1 | 3/2018 | Sutin et al. |
| 2018/0070831 | A1 | 3/2018 | Sutin et al. |
| 2018/0089848 | A1 | 3/2018 | Yang et al. |
| 2019/0025406 | A1 | 1/2019 | Krelboim et al. |
| 2019/0113385 | A1 | 4/2019 | Fukuchi |
| 2019/0175068 | A1* | 6/2019 | Everdell ............ A61B 5/14553 |
| 2019/0192031 | A1 | 6/2019 | Laszlo et al. |
| 2019/0200888 | A1* | 7/2019 | Poltorak ................ G16H 20/70 |
| 2019/0355861 | A1 | 11/2019 | Katnani |
| 2019/0363210 | A1 | 11/2019 | Do Valle |
| 2019/0388018 | A1 | 12/2019 | Horstmeyer |
| 2020/0022581 | A1* | 1/2020 | Vanegas ................ A61B 5/1118 |
| 2020/0041727 | A1 | 2/2020 | Yamamoto |
| 2020/0060542 | A1 | 2/2020 | Alford |
| 2020/0116838 | A1 | 4/2020 | Erdogan |
| 2020/0188030 | A1* | 6/2020 | Kopper .................. A61B 5/745 |
| 2020/0196932 | A1* | 6/2020 | Johnson .................. A61B 5/486 |
| 2020/0253479 | A1 | 8/2020 | Nurmikko |
| 2020/0315510 | A1 | 10/2020 | Johnson |
| 2020/0337624 | A1 | 10/2020 | Johnson |
| 2020/0390358 | A1 | 12/2020 | Johnson |

OTHER PUBLICATIONS

"Partial International Search Report and Invitation to Pay Fees received in International Application No. PCT/2021/018189, dated Jun. 7, 2021".

Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi:10.3390/s18113680, Oct. 29, 2018.

Ban, et al., "Kernel Flow: a high channel count scalable TD-fNIRS system", https://www.spiedigitallibrary.org/conference-proceedings-of-spie Proc. of SPIE vol. 11663, 116630B doi: 10.1117/12.2582888, Mar. 5, 2021.

Ban, et al., "Kernel Flow: a high channel count scalable time-domain functional near-infrared spectroscopy system", https://www.spiedigitallibrary.org/journals/Journal-of-Biomedical-Optics on Jan. 18, 2022.

Contini, et al., "Photon migration through a turbid slab described by a model based on diffusion approximation. I. Theory", Appl. Opt. 36(19), 4587 (1997).

Di Sieno, et al., "Probe-hosted large area silicon photomultiplier and high-throughput timing electronics for enhanced performance time-domain functional near-infrared spectroscopy", Biomed. Opt. Express 11(11), 6389 (2020).

Fishburn, et al., "Temporal Derivative Distribution Repair (TDDR): A motion correction method for fNIRS", Neuroimage. Jan. 1, 2019; 184: 171-179. doi:10.1016/j.neuroimage.2018.09.025.

Huppert, et al., "HomER: a review of time-series analysis methods for near-infrared spectroscopy of the brain", Appl. Opt. 48(10), D280 (2009).

Kienle, et al., "Improved solutions of the steady-state and the time-resolved diffusion equations for reflectance from a semi-infinite turbid medium", J. Opt. Soc. Am. A 14(1), 246 (1997).

(56) References Cited

OTHER PUBLICATIONS

Konugolu, et al., "Broadband (600-1350 nm) Time-Resolved Diffuse Optical Spectrometer for Clinical Use", IEEE Journal of Selected Topics in Quantum Electronics, vol. 22, No. 3, May/Jun. 2016.

Lacerenza, et al., "Wearable and wireless time-domain near-infrared spectroscopy system for brain and muscle hemodynamic monitoring", Biomed. Opt. Express 11(10), 5934 (2020).

Lange, et al., "Clinical Brain Monitoring with Time Domain NIRS: A Review and Future Perspectives", Applied Sciences 9(8), 1612 (2019).

Lange, et al., "MAESTROS: A Multiwavelength Time-Domain NIRS System to Monitor Changes in Oxygenation and Oxidation State of Cytochrome-C-Oxidase", IEEE J. Select. Topics Quantum Electron. 25(1), 1-12 (2019).

Martelli, et al., "Optimal estimation reconstruction of the optical properties of a two-layered tissue phantom from time-resolved single-distance measurements", Journal of Biomedical Optics 20(11), 115001 (Nov. 2015).

Mora, et al., "Fast silicon photomultiplier improves signal harvesting and reduces complexity in time-domain diffuse optics", Opt. Express 23(11), 13937 (2015).

Pifferi, et al., "Performance assessment of photon migration instruments: the MEDPHOT protocol", Applied Optics, 44(11), 2104-2114, 2005.

Prahl, et al., "Optical Absorption of Hemoglobin", http://omlc.ogi.edu/spectra/hemoglobin/index.html, 1999.

Re, et al., "Multi-channel medical device for time domain functional near infrared spectroscopy based on wavelength space multiplexing", Biomed. Opt. Express 4(10), 2231 (2013).

Renna, et al., "Eight-Wavelength, Dual Detection Channel Instrument for Near-Infrared Time-Resolved Diffuse Optical Spectroscopy", IEEE J. Select. Topics Quantum Electron. 25(1), 1-11 (2019).

Torricelli, et al., "Time domain functional NIRS imaging for human brain mapping", NeuroImage 85, 28-50 (2014).

Wabnitz, et al., "Depth-selective data analysis for time-domain fNIRS: moments vs. time windows", Biomed. Opt. Express 11(8), 4224 (2020).

Wabnitz, et al., "Performance assessment of time-domain optical brain imagers, part 1: basic instrumental performance protocol", Journal of Biomedical Optics 19(8), 086010 (Aug. 2014).

Wabnitz, et al., "Performance assessment of time-domain optical brain imagers, part 2: nEUROPt protocol", Journal of Biomedical Optics 19(8), 086012 (Aug. 2014).

Wojtkiewicz, et al., "Self-calibrating time-resolved near infrared spectroscopy", Biomed. Opt. Express 10(5), 2657 (2019).

Zucchelli, et al., "Method for the discrimination of superficial and deep absorption variations by time domain fNIRS", 2013 OSA Dec. 1, 2013 | vol. 4, No. 12 | DOI:10.1364/BOE.4.002893 | Biomedical Optics Express 2893, 2013.

\* cited by examiner

WEARABLE DEVICES AND WEARABLE ASSEMBLIES WITH ADJUSTABLE POSITIONING FOR USE IN AN OPTICAL MEASUREMENT SYSTEM

RELATED APPLICATIONS

The present application is a continuation application of U.S. patent application Ser. No. 17/176,466, filed Feb. 16, 2021, which claims priority under 35 U.S.C. § 119(e) to U.S. Provisional Patent Application No. 63/086,350, filed on Oct. 1, 2020, and to U.S. Provisional Patent Application No. 62/992,552, filed on Mar. 20, 2020, and to U.S. Provisional Patent Application No. 62/979,866, filed on Feb. 21, 2020. These applications are incorporated herein by reference in their respective entireties.

BACKGROUND INFORMATION

Detecting neural activity in the brain (or any other turbid medium) is useful for medical diagnostics, imaging, neuroengineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Optical measurement systems, wearable devices and wearable assemblies for use in optical measurement systems, and methods of positioning wearable devices and wearable assemblies are described herein. For example, an exemplary optical measurement system may include a wearable device including a support assembly configured to be worn on a body of a user and a wearable module assembly supported by the support assembly. The wearable module assembly includes a plurality of light sources configured to emit a plurality of light pulses toward a target within the body of the user and a plurality of detectors each configured to receive a set of photons included in a light pulse included in the plurality of light pulses after the set of photons is scattered by the target. A position of the wearable module assembly on the support assembly is adjustable to a conformable fitting position, as may be required, in order to support the wearable assembly on the desired region-of-interest on the user's head. The optical measurement system may also include a position alignment system configured to facilitate positioning of the wearable module assembly at a same position on the body of the user during different use sessions of the wearable device.

The optical measurement systems and wearable assemblies described herein provide various benefits. For example, the wearable devices described herein allow the position of a wearable module assembly included in a wearable device to be easily adjusted to a desired position to obtain full imaging coverage of a desired region-of-interest on the body of the user. For example, the wearable module assembly may be adjusted to cover a target area of the frontal part of the user's head, a target area in the rear part of the user's head, any combination of cluster areas in the user's head, or coverage in the entire head. Moreover, a wearable module assembly may be independently moved relative to the position of other wearable module assemblies in the wearable device to further enable targeted positioning of multiple regions-of-interest. Additionally, the systems, devices, assemblies, and methods described herein enable consistent positioning of a wearable module assembly at the same location each time the system is worn during a use session. As a result, biological signals (e.g., neural signals) may be reliably and consistently acquired each time the wearable device is worn during a use session. These and other advantages and benefits of the present systems and assemblies are described more fully herein and/or will be made apparent in the description herein.

Figure 1:
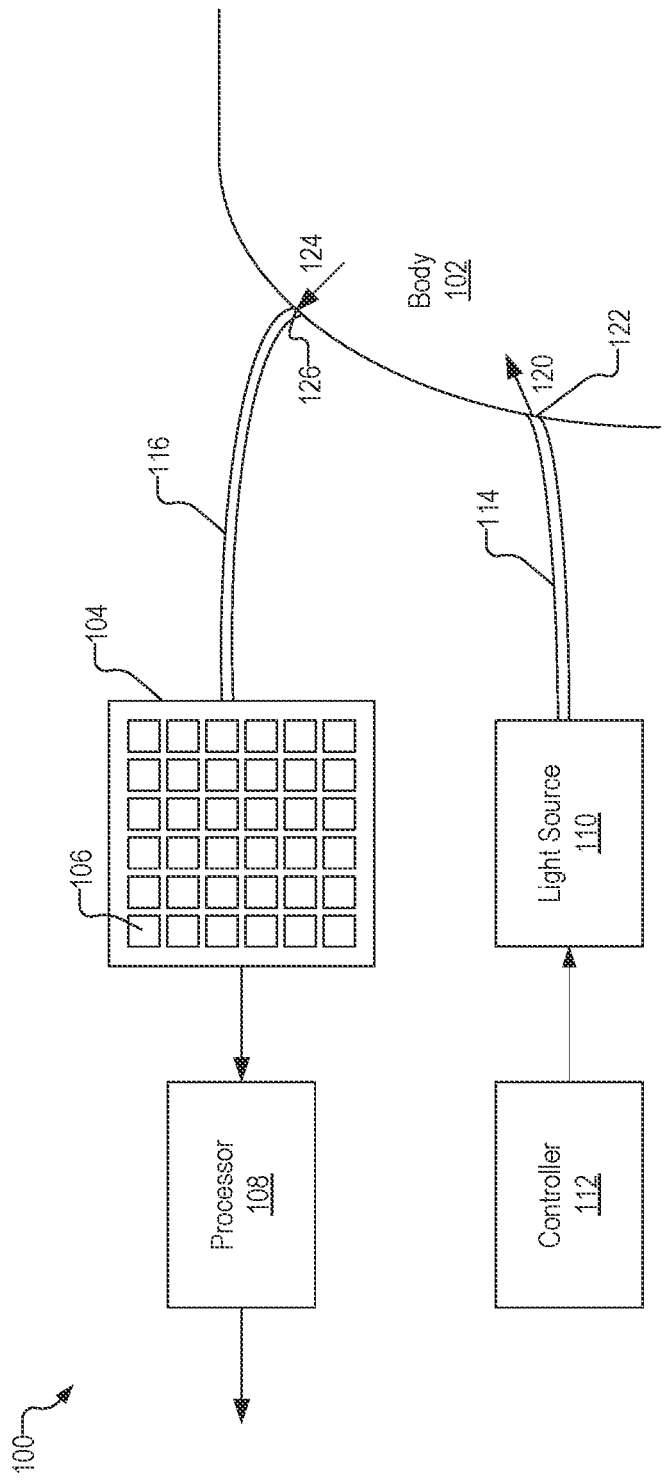
FIG. 1 illustrates an exemplary optical measurement system.

FIG. 1 shows an exemplary optical measurement system 100 configured to perform an optical measurement operation with respect to a body 102. Optical measurement system 100 may, in some examples, be portable and/or wearable by a user.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain digital optical tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light guides, as described more fully herein). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, ..., 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diode (sLEDs), vertical-cavity surface-emitting lasers (VCSELs), titanium sapphire lasers, a micro light emitting diodes (mLEDs), and/or any other suitable laser or light source configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 travels via an optical conduit 114 (e.g., a light pipe, a light guide, a waveguide, a single-mode optical fiber, and/or or a multi-mode optical fiber) to body 102 of a subject. Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., tissue, blood flow, etc.) in body 102. Example embodiments of accumulated outputs are described herein.

Figure 2:
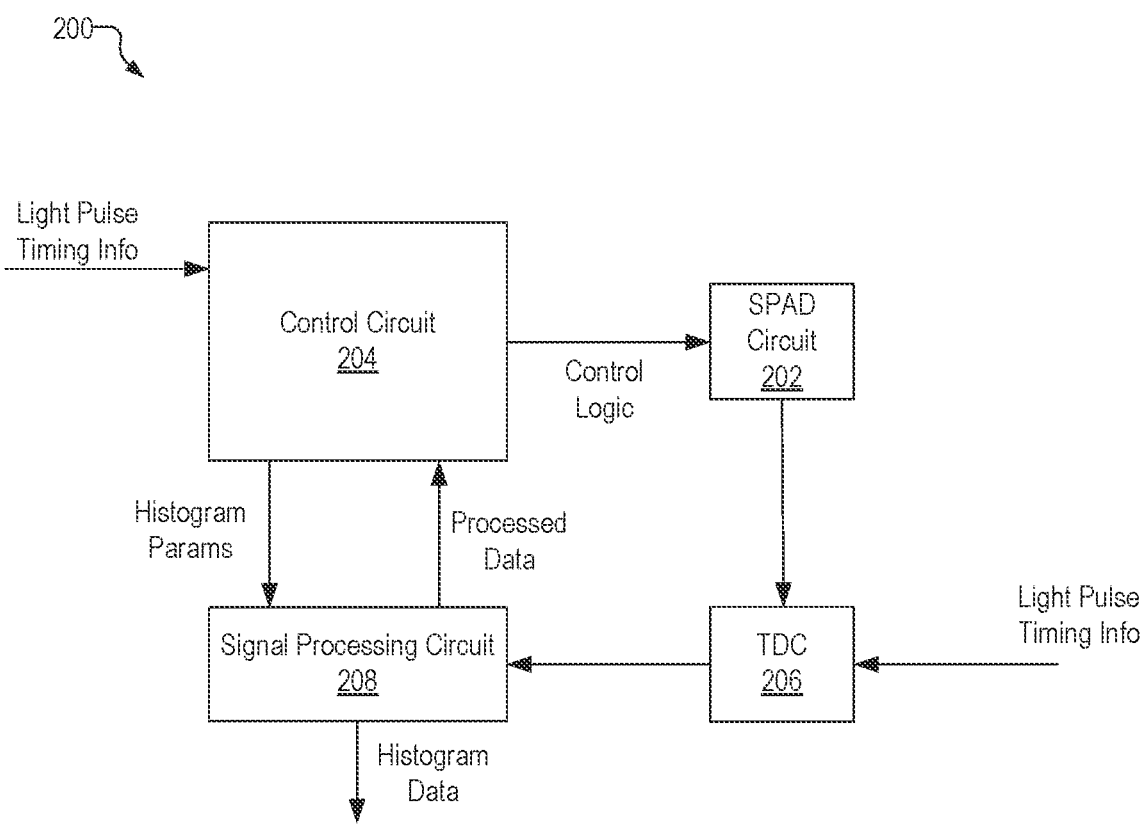
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for one or more SPAD circuits 202 and/or TDCs 206.

Figure 3:
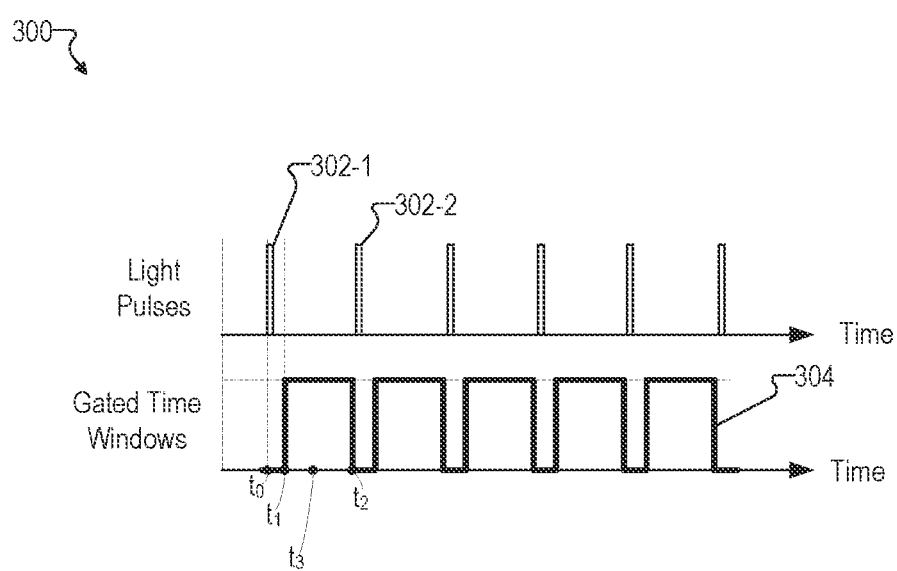
FIG. 3 illustrates an exemplary timing diagram for performing an optical measurement operation using an optical measurement system.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. As shown, light pulse 302-1 is applied at a time t0. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time t0.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

Figure 4:
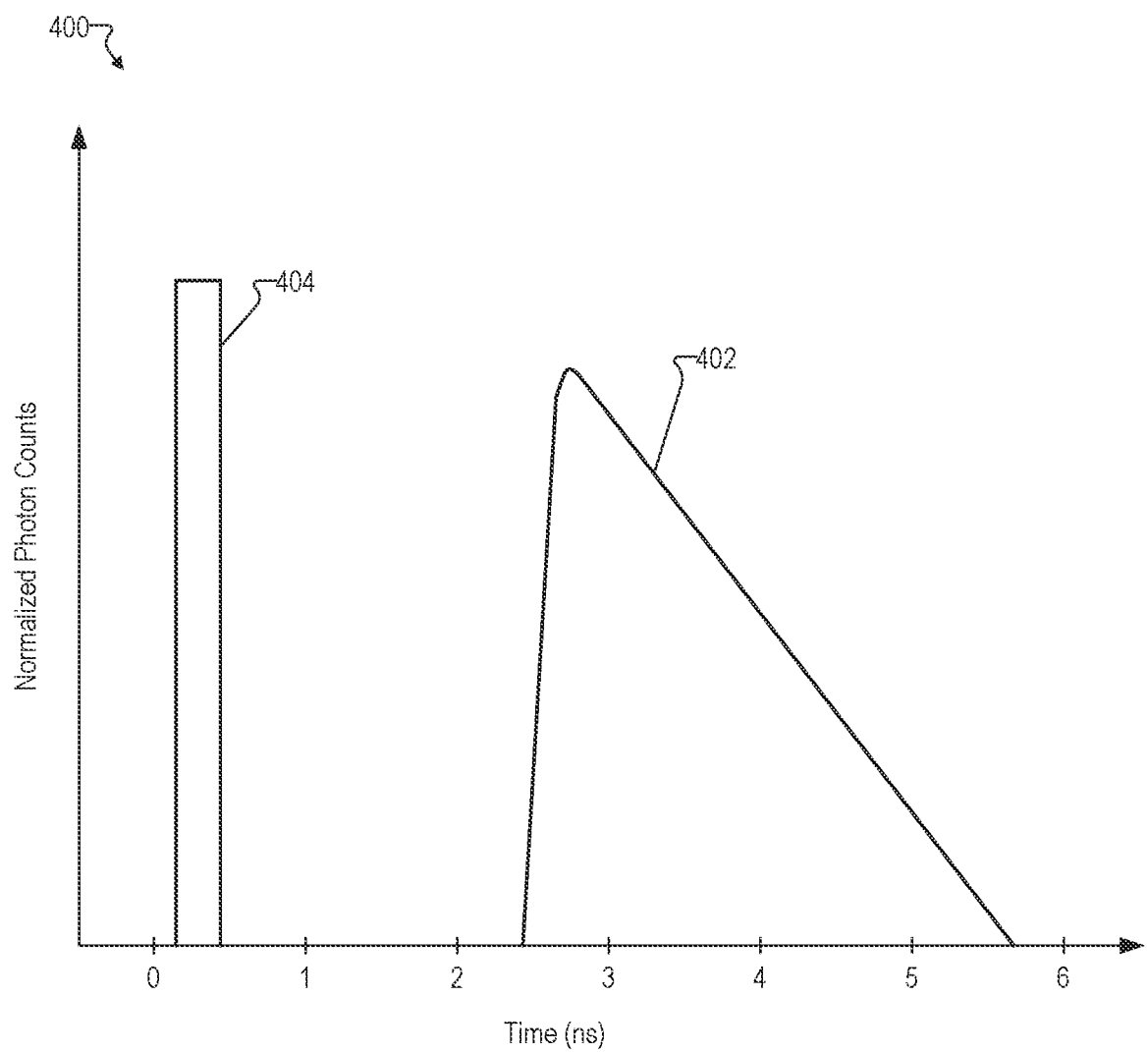
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological (e.g., neural) activity.

Optical measurement system 100 may be implemented by or included in any suitable device(s). For example, optical measurement system 100 may be included in a non-wearable device (e.g., a medical device and/or consumer device that is placed near the head or other body part of a user to perform one or more diagnostic, imaging, and/or consumer-related operations). Optical measurement system 100 may alternatively be included, in whole or in part, in a sub-assembly enclosure of a wearable invasive device (e.g., an implantable medical device for brain recording and imaging).

Alternatively, optical measurement system 100 may be included, in whole or in part, in a non-invasive wearable device that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
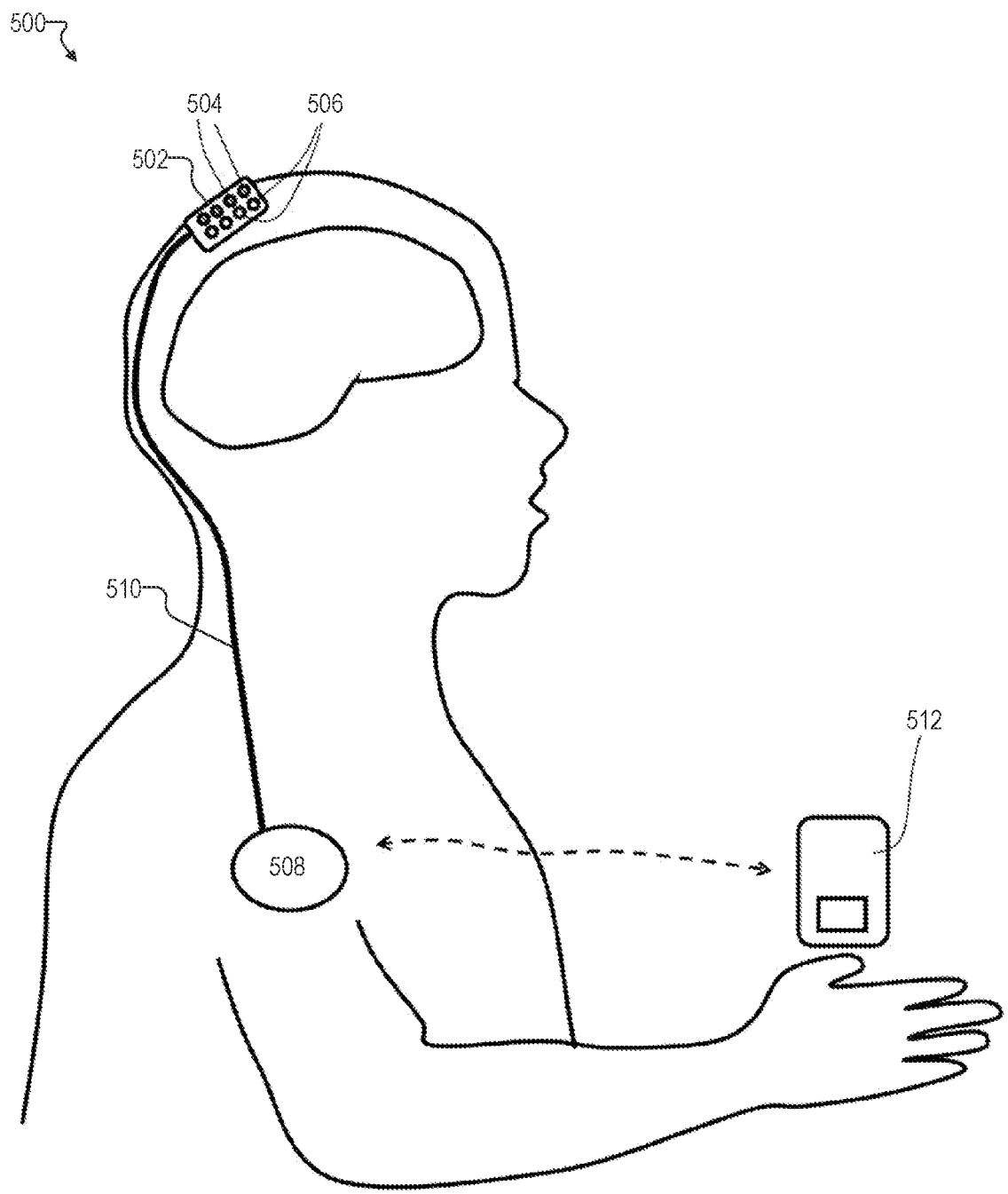
FIG. 5 illustrates an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to and/or worn on a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described below in more detail and in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and/or for transforming photodetector measurements into an intensity value that represents an optical property of a target within the brain. Brain interface system 500 allows optical detection of deep anatomical locations beyond skin and bone (e.g., skull) by extracting data from photons originating from light sources 506 and emitted to a target location within the user's brain, in contrast to conventional imaging systems and methods (e.g., optical coherence tomography (OCT), continuous wave near infrared spectroscopy (CW-NIRS)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506. In some examples, processor 508 is implemented by or similar to processor 108 and/or controller 112.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). In some examples, remote processor 512 is implemented by or similar to processor 108 and/or controller 112.

Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and/or in another wearable or non-wearable device and coupled to head mountable component 502 through an optical connection.

In some alternative embodiments, head mountable component 502 does not include individual detectors 504. Instead, one or more detectors configured to detect the scattered light from the target may be included elsewhere in brain interface system 500. For example, a detector may be included in processor 508 and/or in another wearable or non-wearable device and coupled to head mountable component 502 through an optical connection.

Figure 6:
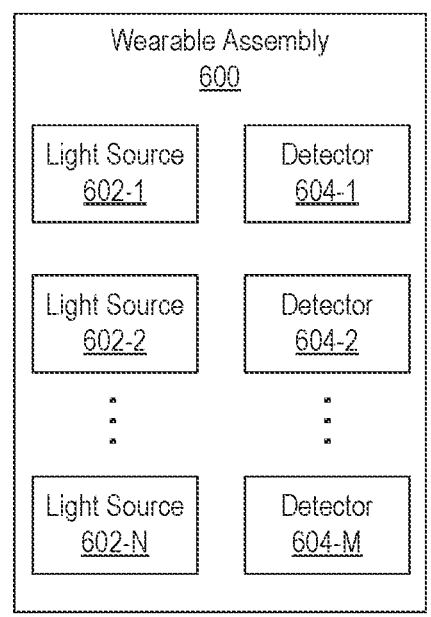
FIG. 6 shows a functional diagram of an exemplary wearable assembly that may implement, or be included in an implementation of, an optical measurement system.

FIG. 6 shows a functional diagram of an exemplary wearable assembly 600 that may implement, or be included in an implementation of, optical measurement system 100. Wearable assembly 600 includes N light sources 602 (e.g., light sources 602-1 through 602-N) and M detectors 604 (e.g., detectors 604-1 through 604-M). Wearable assembly 600 may include any of the other components of optical measurement system 100 as may serve a particular implementation. N and M may each be any suitable value (i.e., there may be any number of light sources 602 and any number of detectors 604 included in wearable assembly 600 as may serve a particular implementation).

Light sources 602 are each configured to emit light (e.g., a sequence of light pulses) and may be implemented by any of the light sources described herein. Detectors 604 may each be configured to detect arrival times for photons of the light emitted by one or more light sources 602 after the light is scattered by the target. For example, a detector 604 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector). Detectors 604 may be implemented by any of the detectors described herein.

Wearable assembly 600 may be implemented by or included in any of the wearable devices, wearable module assemblies, and/or wearable units described herein. For example, wearable assembly 600 may be implemented by or included in a wearable device (e.g., headgear) configured to be worn on a user's head. Wearable assembly 600 may additionally or alternatively be implemented by a wearable device configured to be worn on any other part of a user's body.

Wearable assembly 600 may be modular in that one or more components of wearable assembly 600 may be removed, changed out, or otherwise modified as may serve a particular implementation. Additionally or alternatively, wearable assembly 600 may be modular such that one or more components of wearable assembly 600 may be housed in a separate housing (e.g., module) and/or may be movable relative to other components. Exemplary modular wearable assemblies are described in more detail in U.S. Provisional Patent Application No. 63/081,754, filed Sep. 22, 2020, U.S. Provisional Patent Application No. 63/038,459, filed Jun. 12, 2020, U.S. Provisional Patent Application No. 63/038,468, filed Jun. 12, 2020, U.S. Provisional Patent Application No. 63/038,481, filed Jun. 12, 2020, and U.S. Provisional Patent Application No. 63/064,688, filed Aug. 12, 2020, which applications are incorporated herein by reference in their respective entireties.

Figure 7:
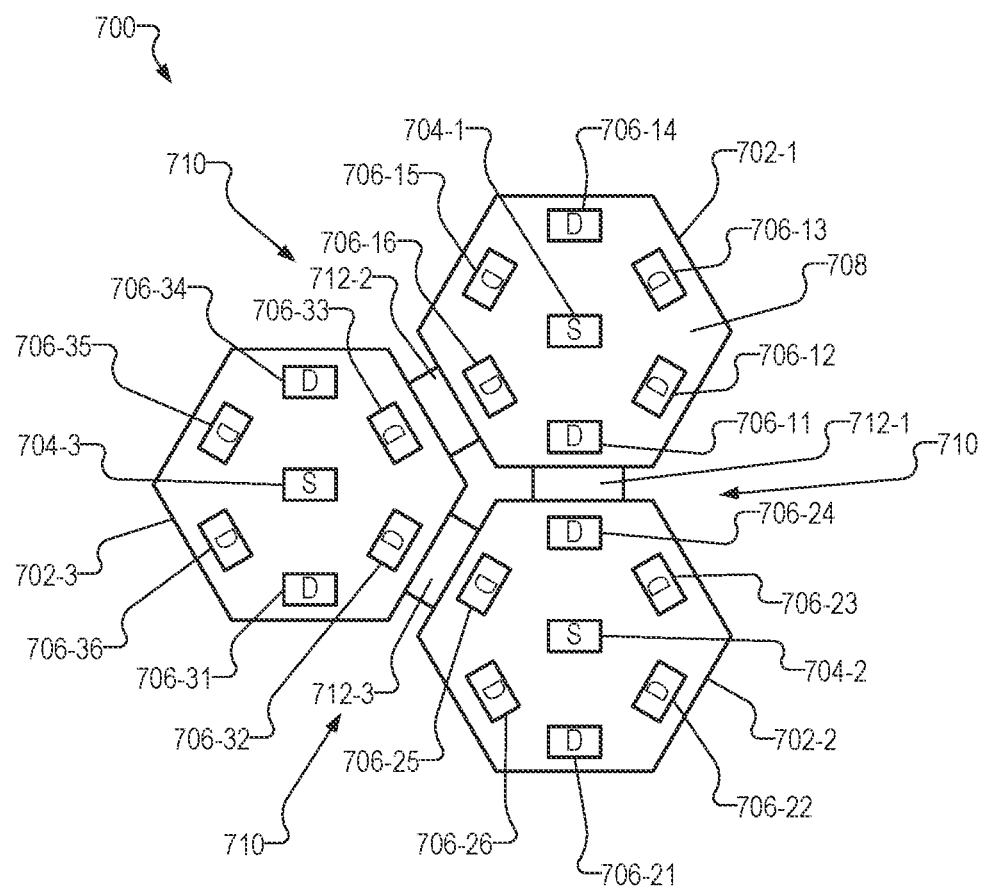
FIG. 7 illustrates an exemplary implementation in which the wearable assembly of FIG. 6 is implemented by a wearable module assembly.

FIG. 7 illustrates an exemplary implementation of a modular wearable assembly. FIG. 7 is illustrative of one of many different implementations of wearable assembly 600 that may be realized in accordance with the principles described herein. As shown in FIG. 7, wearable assembly 600 is implemented by a wearable module assembly 700. Wearable module assembly 700 includes a plurality of wearable modules 702 (e.g., modules 702-1 through 702-3). However, wearable module assembly 700 may alternatively include a single wearable module 702. Module 702-1 can represent or include a first module housing, module 702-2 can represent or include a separate second module housing, module 703-3 can represent or include a separate third module housing, and so forth. While three modules 702 are shown to be included in wearable module assembly 700, in alternative configurations, any number of modules 702 (e.g., a single module up to sixteen or more modules) may be included in wearable module assembly 700.

Each module 702 includes a light source 704 (e.g., light source 704-1 of module 702-1, light source 704-2 of module 702-2, and light source 704-3 of module 702-3) and a plurality of detectors 706 (e.g., detectors 706-11 through 706-16 of module 702-1, detectors 706-21 through 706-26 of module 702-2, and detectors 706-31 through 706-36 of module 702-3). Each module 702 may include any other components as may serve a particular implementation.

In the particular implementation shown in FIG. 7, each module 702 includes a single light source 704 (labeled "S") and six detectors 706 (each labeled "D"). However, each module 702 may have any other number and arrangement of light sources 704 and detectors 706 as may serve a particular implementation. Any one or more components of a module 702 (e.g., a light source 704, detectors 706, and/or any other components) may be housed, in whole or in part, within a module housing.

Each light source 704 may be implemented by any light source described herein and may be configured to emit a light pulse directed at a target (e.g., the brain). For example, light source 704-1 may emit a first light pulse toward the target and light source 704-2 may emit a second light pulse toward the target. In some examples, each light source 704 housed within module 702 includes one or more light-generating components (e.g., laser diodes). Each light source 704 may additionally include any suitable optical components (e.g., an optical conduit) configured to guide and direct emitted light toward the target. In some examples, a portion of each light source 704 (e.g., an optical conduit) protrudes from a front surface 708 of the module 702 (e.g., a surface of module 702 facing, or parallel to a surface of, the body of the user when wearable module assembly 700 is worn by the user) to facilitate contact of light source 704 with the body of the user and/or to penetrate through the user's hair.

Each light source 704 may be located at a center region of front surface 708. In alternative implementations, a light source 704 of a module 702 may be located at any other location on the module. In alternative configurations (not shown) of a module 702, one or more components of the light source 704 (e.g., laser diodes) may be located remotely in/on another device separate from module 702, and the generated light may be conveyed to module 702 by another optical conduit (e.g., optical fibers, etc.).

Each detector 706 may be implemented by any detector described herein and may include a plurality of photodetectors (e.g., SPADs) as well as other circuitry (e.g., TDCs, RF antennas, inductive coupling coils) housed within module 702. Each detector 706 may be configured to detect arrival times for photons of the light emitted by one or more light sources after the photons are scattered by the target. For example, detector 706-11 may detect a first set of photons included in the first light pulse after the first set of photons are scattered by the target, and detector 706-21 may detect a second set of photons included in the second light pulse after the second set of photons are scattered by the target. In some examples, each detector 706 housed within module 702 may also include any suitable optical components (e.g., an optical conduit) configured to receive and guide photons scattered by the target toward the plurality of photodetectors included in the detector 706. In some examples, a portion of each detector 706 (e.g., an optical conduit) protrudes from front surface 708 to facilitate contact with the body of the user and/or to penetrate through the user's hair.

In alternative configurations (not shown) of a module 702, one or more components of a detector 706 (e.g., a photodetector) may be located remotely in/on another device separate from the module 702, and the scattered photons received by detector 706 are conveyed from the module 702 by another optical conduit (e.g., optical fibers, etc.) to the remote component.

Wearable module assembly 700 also includes a connecting assembly 710 that physically connects individual modules 702 with one another. In some examples, connecting assembly 710 flexibly connects modules 702 such that wearable module assembly 700 is conformable to a 3D (non-planar) surface, such as a surface of the user's body (e.g., the user's head), when the wearable module assembly 700 is worn by the user.

Connecting assembly 710 may be implemented by any suitable device, structure, connectors, or mechanism as may suit a particular implementation. For example, as shown in FIG. 7, connecting assembly 710 is implemented by a plurality of connectors 712 (e.g., connectors 712-1 to 712-3) between adjacent modules 702. In additional or alternative configurations, connecting assembly 710 may be implemented by a common support assembly that indirectly connects modules 702. The common support assembly may include, for example, an open-mesh (e.g., web-like) structure, a closed-surface structure (e.g., a flex circuit), and/or any other suitable assembly.

In the examples described above, wearable modules 702 included in wearable module assembly 700 operate in accordance with a time-domain optical measurement modality (e.g., TD-NIRS). In other examples, wearable module assembly 700 may include one or more auxiliary modules that operate in accordance with a different measurement modality, such as continuous wave NIRS (CW-NIRS), frequency-domain NIRS (FD-NIRS), electroencephalography (EEG), electromyography (EMG), magnetoencephalography (MEG), positron emission tomography (PET), functional magnetic resonance imaging (fMRI), single-photon emission computed tomography (SPECT), functional ultrasound imaging (fUS), and any other imaging modality as may serve a particular implementation.

As mentioned above, wearable assembly 600 (e.g., wearable module assembly 700) may be included in or implemented by a wearable device that may be worn on a body of a user. Exemplary wearable devices will now be described. In the examples that follow the wearable devices are described as headgear configured to be worn on a user's head. However, the wearable devices may have any other suitable form and may be configured to be worn on any other part of a user's body as may serve a particular implementation.

Figure 8A:
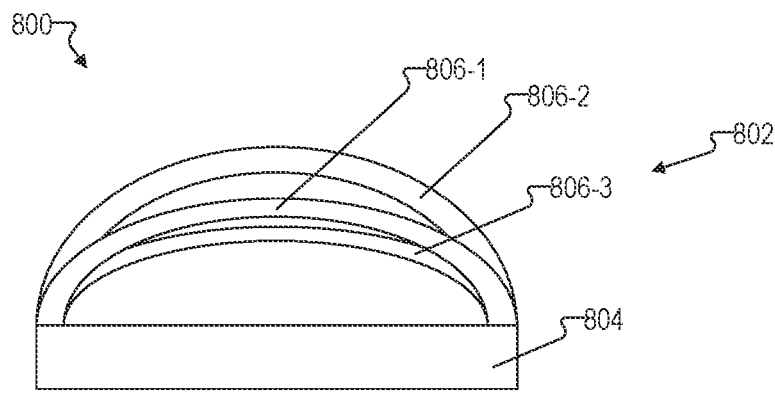
FIGS. 8A to 8C illustrate an exemplary wearable device configured to be worn on a head of a user.
Figure 8B:
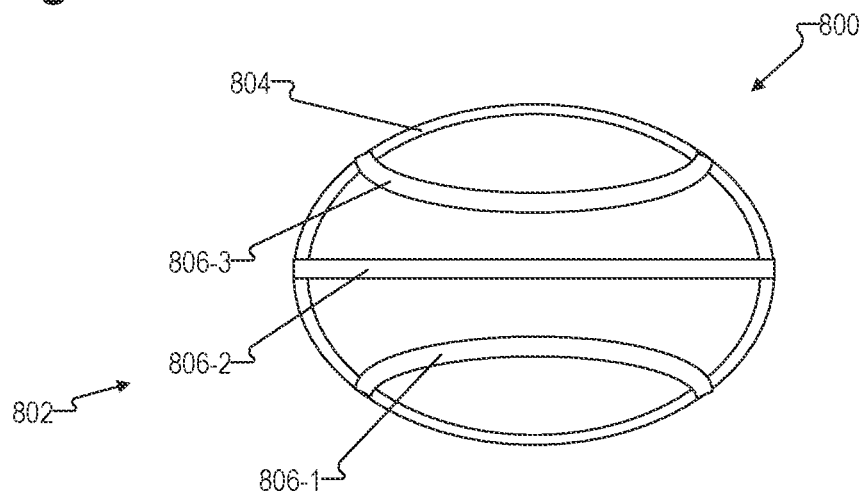
Figure 8C:
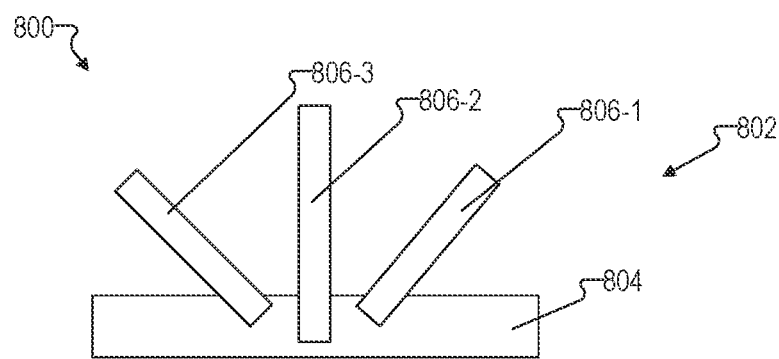
Figure 9A:
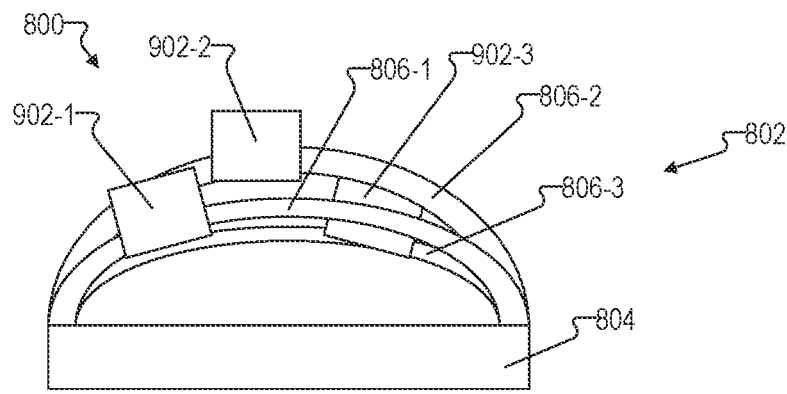
FIGS. 9A to 9C illustrate the exemplary wearable device of FIGS. 8A to 8C with a plurality of wearable assemblies.
Figure 9B:
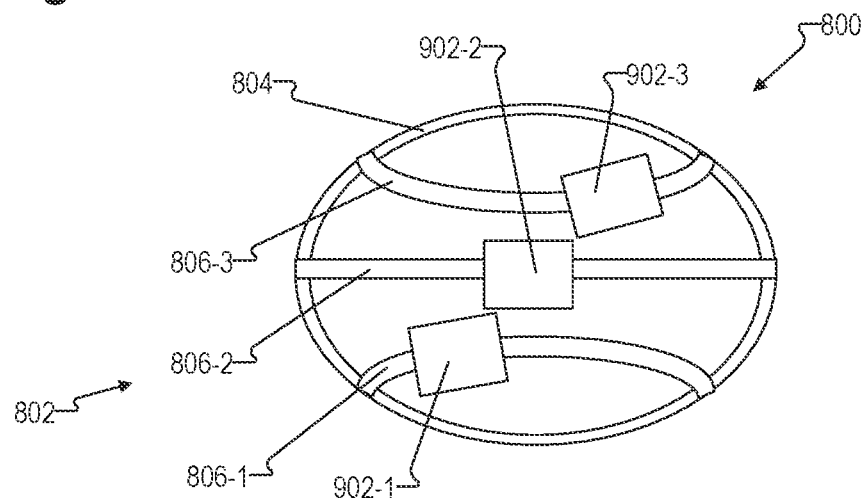
Figure 9C:
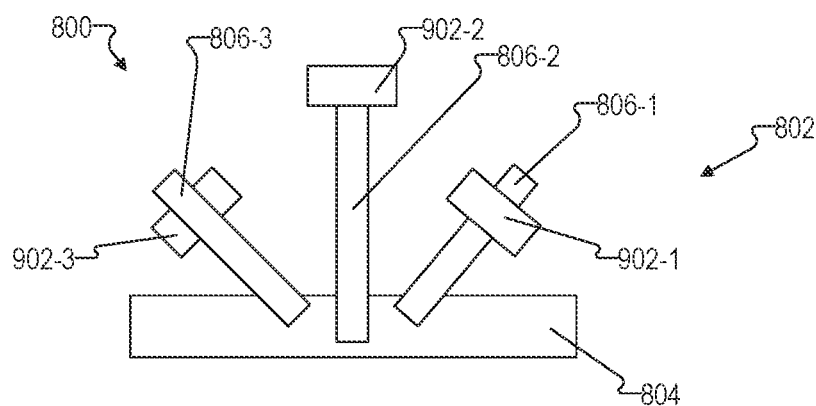

FIGS. 8A to 9C illustrate an exemplary wearable device 800 configured to be worn on a head of a user. FIG. 8A shows a side view of wearable device 800, FIG. 8B shows a top view of wearable device 800, and FIG. 8C shows a front view of wearable device 800. As shown in FIGS. 8A to 8C, wearable device 800 includes a support assembly 802 configured to support a wearable assembly (not shown), such as wearable assembly 600 or wearable module assembly 700. FIGS. 9A to 9C show wearable device 800 with a plurality of wearable assemblies 902 (e.g., wearable assemblies 902-1 to 902-3) supported on support assembly 802. While FIGS. 9A to 9C show three wearable assemblies 902, wearable device 800 may include any other number of wearable assemblies 902 as may serve a particular implementation. Wearable device 800 may also include any other components as may serve a particular implementation.

Support assembly 802 is configured to be worn on the body of the user and support (e.g., hold) each wearable assembly 902 (see FIGS. 9A-9C) over a region-of-interest on the user's body. Support assembly 802 includes a body support portion 804 and a plurality of support members 806 (e.g., support member 806-1 to 806-3). Body support portion 804 is configured to rest on, or be supported by, the user's body. For example, as shown in FIGS. 8A-9C, body support portion 804 is in the form of a headband configured to be worn around a user's head. However, body support portion 804 may have any other suitable shape or configuration that allows body support portion 804 to be worn on and/or conform to the user's head or body (e.g., earpieces, nosepiece, etc.). Body support portion 804 may be formed of any suitable material and may be flexible or rigid as may serve a particular implementation. In some examples, body support portion 804 is adjustable to achieve a desired fit on the user's head.

As shown in FIGS. 9A-9C, each support member 806 is configured to support (e.g., hold, maintain, etc.) one or more wearable assemblies 902 over a target (e.g., the brain) within the user's body. Each support member 806 is connected at both ends to body support portion 804 and crosses over a portion of the user's head when support assembly 802 is worn on the head. While FIGS. 8A-9C show that support assembly 802 includes three support members 806, support assembly 802 may have any other suitable number of support members 806 (e.g., one, two, or more than three). Moreover, while FIGS. 8A-9C show that support members 806 extend from the front of body support portion 804 (e.g., a portion that is worn near the user's forehead) to the back of body support portion 804 (e.g., a portion that is worn near the back of the user's head), support members 806 may be connected to body support portion 804 at any other suitable locations. In some examples, support members 806 extend from a left side to a right side of body support portion 804.

In yet further examples, support assembly 802 includes crossing or interconnected support members, such as a set of support members 806 that extend from front to back and another set of support members 806 that extend from left to right to form a web-like structure.

Support members 806 may be formed of any suitable material and may be flexible, elastic, or rigid. For example, support members 806 may be implemented by elastic cords, flexible nylon straps, rigid rails, or a combination of these. Support members 806 may be connected to body support portion 804 by any suitable connection mechanisms, such as but not limited to buttons, hook-and-loop fasteners, buckles, snaps, rings, grommets or slits in body support portion 804, clamps, worm gears, ratchets, clips, ties, elastic bands, screws or fasteners, cord locks, toggles, spring locks, stoppers, and the like. In some examples, support members 806 are permanently connected to body support portion 804. For instance, support members 806 may be integrally formed with body support portion 804.

In additional or alternative examples, support members 806 are adjustably connected to body support portion 804. For example, one or more of a position, length, or tension of a support member 806 may be adjustable. To illustrate, the position of a support member 806 relative to body support portion 804 may be adjustable by changing the location on body support portion 804 where support member 806 is connected to body support portion 804. For example, body support portion 804 may include a plurality of connection locations (e.g., buttons, snaps, hooks, etc.) at which support member 806 may be connected. The position of support member 806 may additionally or alternatively be adjusted by pivoting support member 806 about its connection point with body support portion 804. As another example, the position of support member 806 may be adjusted by adjusting one or more bands or other support members 806 that are connected to the support member (e.g., at a location between connection points with body support portion 804). The length of support member 806 may be adjusted by changing the length of support member 806 between connection points on body support portion 804. For instance, support member 806 may be a flexible strap and the length of the strap between connection points on body support portion 804 may be adjusted by means of an adjustable buckle or cord lock. As another illustration, the length of support member 806 may be adjusted by pushing or pulling a back portion of support member 806 through a locking mechanism (e.g., a ratchet or worm gear). The tension of an elastic support member 806 may also be adjusted to shorten or elongate the support member 806.

Each wearable assembly 902 may be supported by support members 806 in any suitable way. In some examples, a wearable assembly 902 is permanently or non-movably held or supported by one or more support members 806. Alternatively, the wearable assembly 902 may be adjustably connected to one or more support members 806 such that the wearable assembly 902 may change position along support member 806 or may rotate about a connection point with support member 806. For instance, wearable assembly 902-1 may include one or more connectors that movably engage with support member 806-1 to adjustably hold wearable assembly 902-1 on support member 806-1. The connectors may be implemented by any suitable devices or mechanisms, such as hoops, hooks, rings, grooves, cord locks, and/or any other device or mechanism. Alternatively, wearable assembly 902 may be connected to support members 806 by adjustable fasteners (e.g., screws, hook-and-loop fasteners, etc.). In some examples, the position of wearable assembly 902 on support member 806 may be locked by a locking mechanism (e.g., a cord lock, a tension lock, a friction lock, etc.). In yet further examples, wearable assembly 902 may be movably connected to a support member 806 by way of a carriage (not shown) that is movably connected to support member 806 and that is configured to hold wearable assembly 902.

Each wearable assembly 902 may be connected to a support member 806 by way of a wearable module (e.g., a module 702) included in the wearable assembly and/or by way of a connecting assembly (e.g., connecting assembly 710) that connects or supports a plurality of wearable modules together in a wearable module assembly (e.g., wearable module assembly 700).

As mentioned, in some examples support members 806 may be implemented by rails. A rail, body support portion 804 to which the rail is connected, and/or a wearable assembly 902 supported by the rail may use a ratchet and pawl type mechanism, a lead-screw, pulleys and gears/wheels, treads and sprockets, friction locks, screw locks, or any other mechanisms or devices, or combination thereof, for adjusting the rail and/or wearable assembly 902 supported by the rail. In some examples, the rails may include marks or other means of positional indication including rotary encoders, linear encoders, strain gauges, RF antennas, magnets, or combination thereof, for indicating the various positions along the rails. In this way, the length of a rail and the position of wearable assembly 902 on the rail can be identified and repeated, as necessary. The rails may also indicate marks, rotary encoders, or any other means of angular indication to indicate the angle of the rails relative to body support portion 804 or some other reference member.

Adjustment of support member 806 and/or wearable assemblies 902 can be made manually, automatically, and/or with assistance from motorized mechanisms. For example, a motorized mechanize may be configured to pull support members 806 to preset locations. The preset locations may be based on a known mechanical encoding or similar ratcheting feature for knowing how much of the support member 806 has been pulled. Alternatively, a support member 806 could be pulled until a certain level of tension is reached, as determined by an attached sensor. Control circuitry may be used to provide control of the mechanical support members 806 such that the coupling is optimized as determined by online analysis of signal-to-noise ratio or other metric. In some examples, different users could share a device with each user having a different preset configuration that is stored in non-volatile memory on the device.

In some examples, support members 806 are configured to conform to the user's body (e.g., head). For instance, flexible and/or elastic bands may be configured to be stretched or pulled tight to bring wearable assembly 902 (e.g., light emitters and light receivers) into contact with the user's head. Rigid rails may be shaped (e.g., curved) to conform to the shape of the user's head. As a result, support assembly 802 is configured to pull each wearable assembly 902 tight against the user's head, thereby ensuring better coupling to the tissue for signal acquisition from the target. Some wearable devices may include a combination of the conformal and rigid type systems. For example, a rigid body support portion 804 may be combined with flexible or elastic support members 806, and vice versa.

In some examples, support members 806 may support wearable units, devices, or modules of measurement modalities different from time-domain optical modalities (e.g., EEG, EKG, EMG, MEG, EOG, eye/pupil tracking, etc.) for detecting or recording brain signals or other biological signals from the user.

Support assembly 802 also allows wearable assemblies 902 (e.g., wearable modules 702 in wearable module assemblies 700) to be packed in any desired configuration by the positioning of support members 806 and/or wearable assemblies 902 on support members 806. For example, support members 806 may be sparsely populated across the rigid structure, or may be positioned in close proximity to one another to allow for densely packing modules together in clusters for higher signal fidelity acquisition. Support members 806 may be added or removed as needed based on the desired use case, or may be permanently incorporated into support assembly 802.

With the configurations of support assembly 802 describe herein, a position of wearable assembly 902 on support assembly 802 may be adjustable. That is, a location of wearable assembly 902 in a three-dimensional space relative to body support portion 804 or a support member 806 that supports wearable assembly 902 is adjustable. Thus, when wearable device 800 is worn by a user, the position of wearable assembly 902 may be adjusted to cover a desired region-of-interest. In some examples, the region-of-interest is a particular functional region of the brain, such as the cerebrum, the cerebellum, the cerebral cortex, a particular lobe (e.g., frontal lobe, parietal lobe, occipital lobe, temporal lobe, anterior lobe, posterior lobe, flocculonodular lobe, etc.) or a particular area within a lobe or other brain region (e.g., Wernicke's Area, Broca's Area, prefrontal cortex, the visual area, the motor function area, etc.). The position of wearable assembly 902 may be adjusted so that the entire functional region of the brain is imaged by the optical measurement system. In examples in which wearable device 800 includes multiple different wearable assemblies 902, wearable assemblies 902 may also be movable relative to one another. In this way, each wearable assembly 902 can be positioned to target a different region-of-interest and/or to accommodate different user head morphologies.

Figure 10:
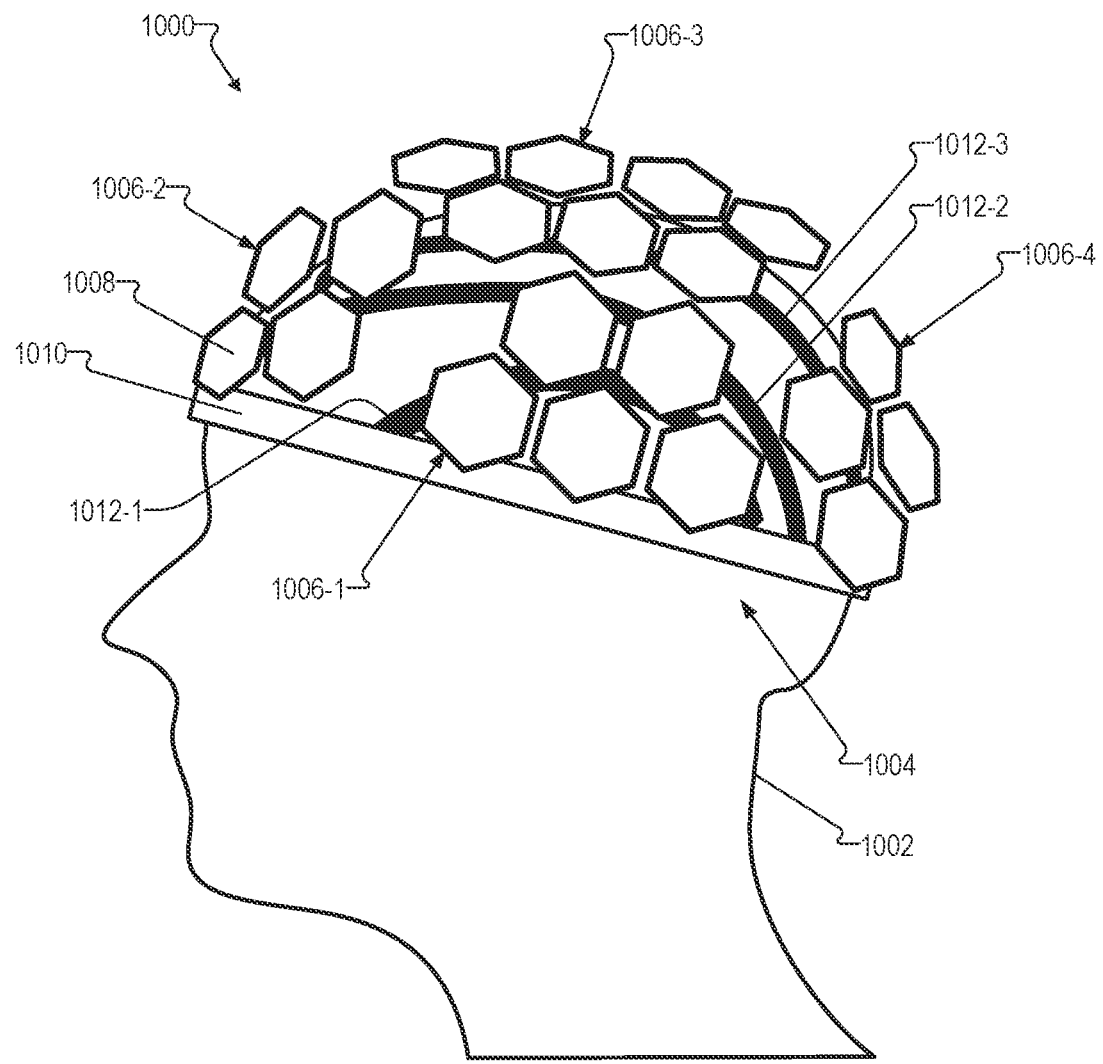
FIGS. 10 and 11 show side views of an exemplary wearable device as worn on a head of a user.

The adjustability of wearable assemblies 902 will be illustrated with reference to FIGS. 10 and 11. FIG. 10 shows a side view of an exemplary wearable device 1000 as worn on a head 1002 of a user. Wearable device 1000 includes a support assembly 1004 supporting a plurality of distinct wearable module assemblies 1006 (e.g., wearable module assemblies 1006-1 through 1006-4). Each wearable module assembly 1006 may be implemented, for example, by wearable module assembly 700 and includes a plurality of wearable modules 1008 (e.g., wearable modules 702). For example, FIG. 10 shows five wearable modules 1008 grouped together to form wearable module assembly 1006-1 and the five wearable modules 1008 are positioned on a desired region-of-interest on the user's head 1002.

Support assembly 1004 includes a body support portion 1010 and a plurality of support members 1012 (e.g., support members 1012-1 through 1012-3). Support member 1012-1 supports wearable module assembly 1006-1, support member 1012-2 supports wearable module assembly 1006-2, and support member 1012-3 supports wearable module assemblies 1006-3 and 1006-4. As shown in FIG. 10, support members 1012 are positioned beneath wearable module assemblies 1006 (i.e., positioned between wearable module assemblies 1006 and head 1002 of a user. In alternative configurations, support members 1012 may be positioned on top of wearable module assemblies 1006.

Figure 11:
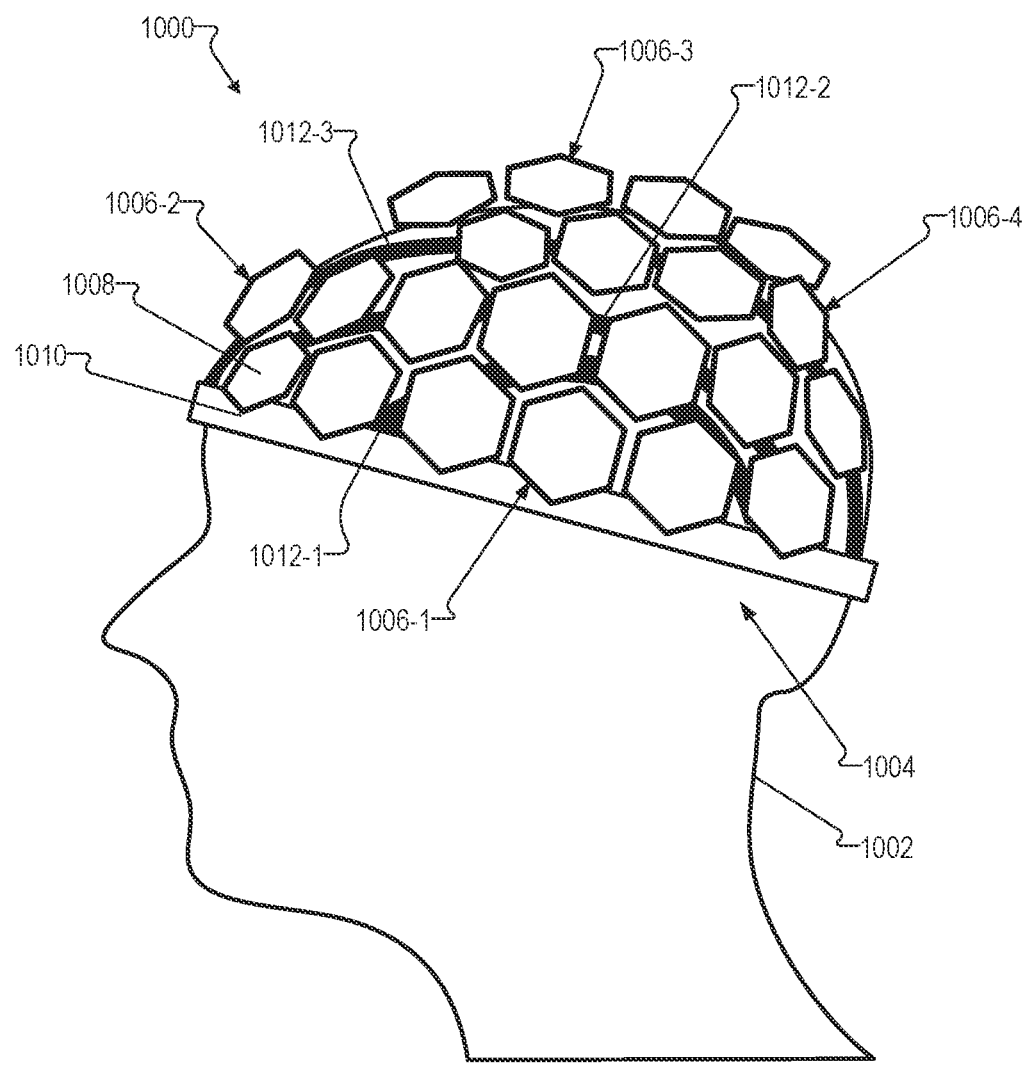

FIG. 11 shows a side view of wearable device 1000 after wearable module assemblies 1006 have been adjusted. As shown in FIG. 11, a position of each wearable module assembly 1006 has been adjusted on support assembly 1004 and relative to each of the other wearable module assemblies 1006 and relative to the desired region-of-interest on the user's head 1002. Accordingly, wearable module assemblies 1006 have been re-positioned to achieve more spatially uniform and expansive coverage of a desired region-of-interest.

In some examples, a wearable device may include a pressing member configured to press the wearable assemblies supported by the support assembly into contact with the user's body when the wearable device is worn on the body of the user. The pressing member may include, for example, an elastic band, a strap, a hat or cap, an inflatable bag within a helmet, a liquid filled flexible shell/bag, springs, permanent magnets, electromagnets, or any other suitable device configured to press, to a conformable fitting position as may serve a particular use session, the wearable assembly against the body surface. For instance, the helmets shown in FIGS. 19 and 20 may cover and press a wearable assembly 600 against the user's head to a conformable fitting position, as may be required, in order to support the wearable assembly on the desired region-of-interest on the user's head. In some examples, the fit of the helmets is adjustable to produce the pressing force. Thus, the pressing member may help maintain light sources 602 and detectors 604 in contact with the body surface.

Figure 12:
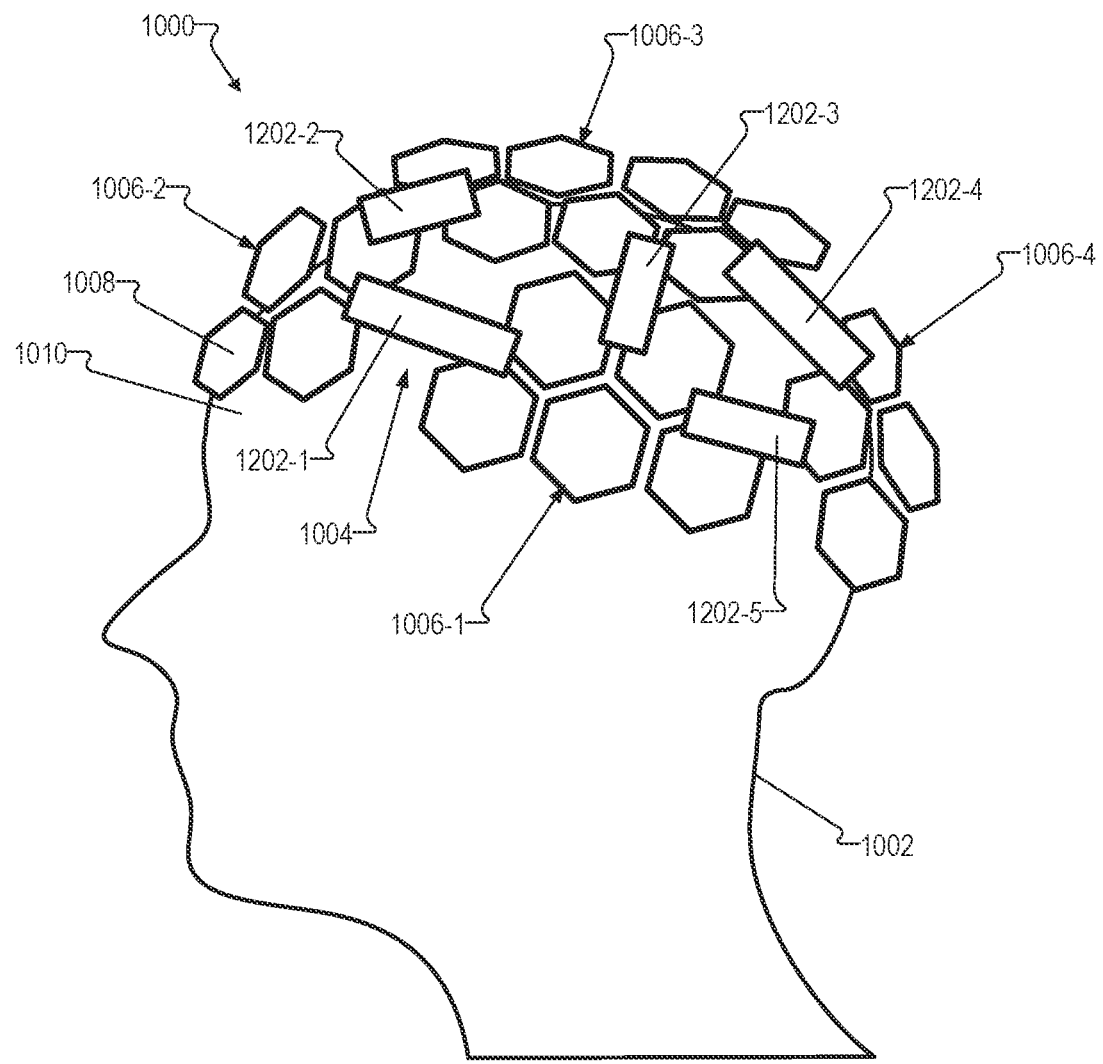
FIG. 12 shows a side view of another exemplary wearable device as worn on a head of a user.

In the embodiments described above, support assembly 802 includes a body support portion 804 and one or more support members 806 connected to body support portion 804. In alternative embodiments, support assembly 802 comprises a plurality of support members 806 that directly interconnect different wearable assemblies 902, as illustrated in FIG. 12. FIG. 12 is similar to FIG. 10 except that in FIG. 12 support assembly 1004 comprises a plurality of assembly connectors 1202 (e.g., assembly connectors 1202-1 to 1202-5) that interconnect wearable module assemblies 1006. For example, assembly connector 1202-1 connects wearable module assembly 1006-1 to wearable module assembly 1006-2, assembly connector 1202-2 connects wearable module assembly 1006-2 to wearable module assembly 1006-3, and so on.

Assembly connectors 1202 may be implemented by any suitable connecting mechanism, including any connecting mechanism described herein. Assembly connectors 1202 may connect adjacent wearable module assemblies 1006 by way of any wearable module 1008 and/or connecting assembly (not shown) included in the wearable module assemblies 1006. Assembly connectors 1202 may be adjustable to thereby facilitate adjustment of positions of wearable module assemblies 1006 relative to one another and relative to the target. For example, assembly connectors 1202 may be implemented by adjustable straps and side-release buckles. Accordingly, a length of assembly connectors 1202 may be lengthened or shortened as desired to adjust positions of wearable module assemblies 1006.

As shown in FIG. 12, support assembly 1004 does not include body support portion 804. However, in some embodiments (not shown) support assembly 1004 may include body support portion 1010 and wearable module assemblies 1006 may also be connected to body support portion 1010 by way of one or more additional connectors.

Figure 13A:
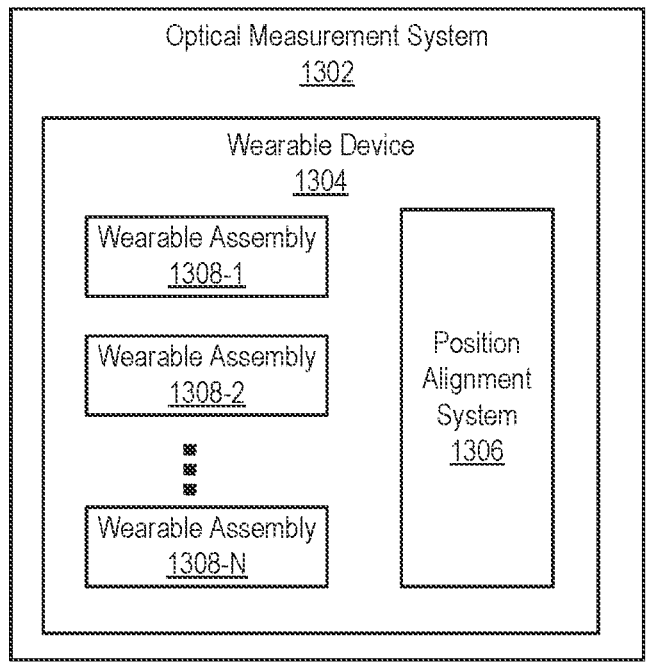
FIGS. 13A and 13B illustrate exemplary configurations of an exemplary optical measurement system that includes a position alignment system.
Figure 13B:
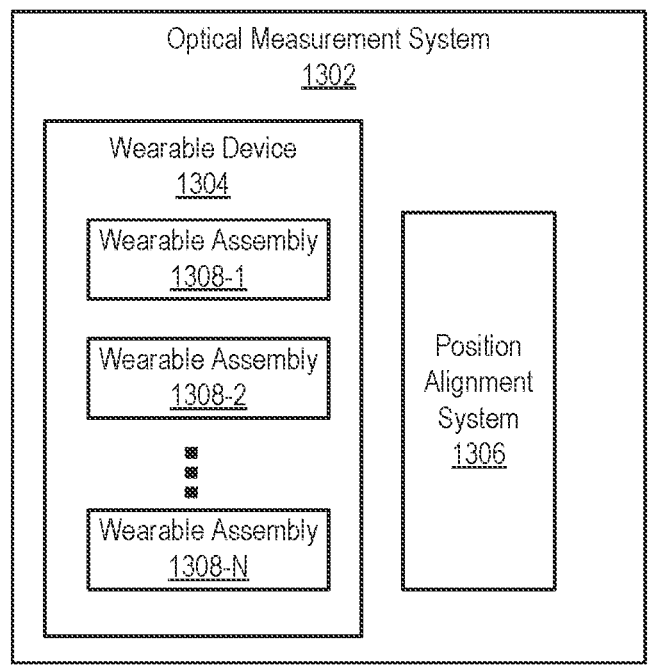

In some scenarios, it may be important to position the wearable device and/or the wearable assemblies included in the wearable device at the same position on the user's body and/or relative to the desired region-of-interest during multiple different use sessions. Consistent placement enables the repeatable acquisition of consistent data across different use sessions that can be easily compared and analyzed. In some examples, optical measurement systems described herein (e.g., optical measurement system 100) may include a position alignment system configured to facilitate consistent positioning of a wearable device, wearable assembly, wearable module assembly, and/or wearable module on the user's body during different use sessions. For example, FIGS. 13A-13B show illustrative configurations 1300-1 and 1300-2 of an exemplary optical measurement system 1302 in accordance with the principles described herein.

Optical measurement system 1302 may be an implementation of optical measurement system 100 and, as shown, includes a wearable device 1304 and a position alignment system 1306. Wearable device 1304 may be implemented by any wearable device described herein (e.g., wearable device 800 or 1000) and may include any one or more wearable assemblies 1308 (e.g., wearable assemblies 1308-1 to 1308-N) described herein. Position alignment system 1306 may implement any mechanical-based, sensor-based, and/or signal-based devices and/or operations to obtain consistent positioning of wearable device 1304 and/or wearable assemblies 1308. Optical measurement system 1302 may also include any other components as may serve a particular implementation.

In configuration 1300-1, position alignment system 1306 is integrated in wearable device 1304 (e.g., in a housing of a module 702, in or on support assembly 802, etc.), as will be described below in more detail. In configuration 1300-2, position alignment system 1306 is not integrated in wearable device 1304. For example, position alignment system 1306 may be included in a wearable device separate from wearable device 1304 (e.g., a mobile device). In some configurations (not shown), position alignment system 1306 is distributed across components included in both wearable device 1304 and components located remotely from wearable device 1304. In alternative configurations (not shown), position alignment system 1306 is not included in optical measurement system 1302 but is a standalone system that is physically and electrically unconnected with optical measurement system 1302.

Figure 14A:
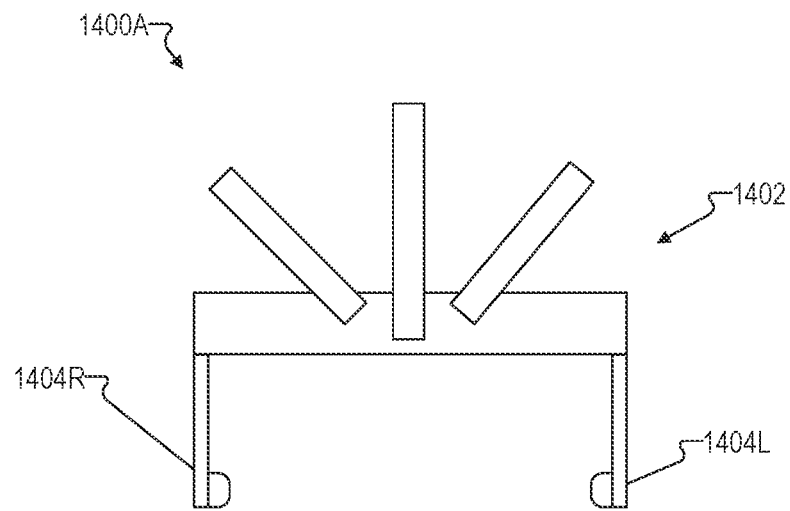
FIGS. 14A and 14B illustrate exemplary implementations of a wearable headset including a body engagement member.
Figure 14B:
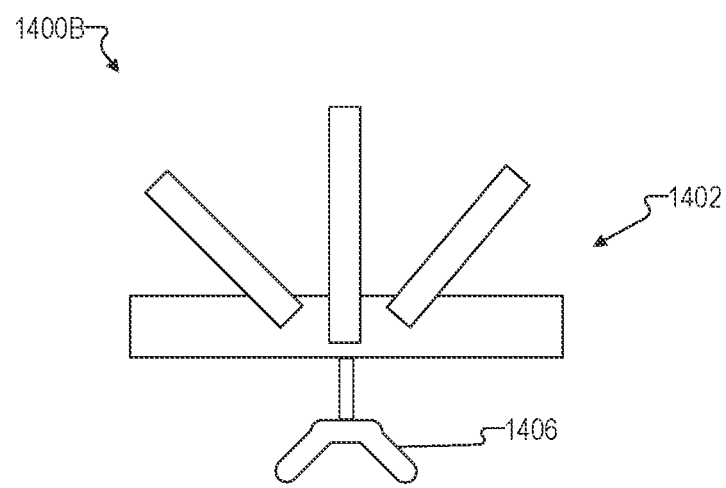

As mentioned, position alignment system 1306 may implement mechanical devices and alignment methods. In such examples, wearable device 1304 may include one or more body engagement members configured to engage with (e.g., rest on, touch, fit into, etc.) anatomical features of the user's body to facilitate consistent placement of the wearable device on the user's body. The body engagement members may be connected to a support assembly of wearable device 1304 (e.g., support assembly 802). To illustrate, as shown in FIG. 14A, a wearable headset 1400A includes a support assembly 1402 and right and left earpieces 1404R and 1404L connected to support assembly 1402 and configured to rest in the user's ears (e.g., in the outer ear canal). As another example (not shown), earpieces 1404 may include ear cups that rest on or envelope the ears. In another example shown in FIG. 14B, a wearable headset 1400B includes a nosepiece 1406 connected to support assembly 1402 and configured to rest on the bridge of the user's nose.

It will be recognized that earpieces 1404 and nosepiece 1406 are merely illustrative, as the body engagement members may take any other suitable form and may engage with any other feature of the user's body. For example, a body engagement member may include a structure (e.g., a ring, a band, a pad, etc.) configured to rest on the user's inion at the back of the user's head. As another example, the body engagement member may include a chinstraps configured to engage with the user's body under the chin. In some examples, wearable device 1304 may have three or more points of contact with anatomical features (e.g., both ears and the nose bridge), thereby improving accuracy in consistent placement. Expanded foam or molded padding may also be used and configured to engage with the user's body where needed for repeatable positioning and position maintenance.

In some examples, the body engagement members are adjustable so that they may be customized for a particular user. The position of the body engagement members may be indicated by markings on the body engagement members or support assembly. The body engagement members may be locked when the appropriate fit is set to prevent misalignment during use and so that the same fit may be achieved during each subsequent use session. Additionally or alternatively, the body engagement members may be removed after appropriate positioning to improve comfort and convenience for the user.

In some examples, a wearable device may implement a custom-fit body engagement member that engages with an anatomical feature of the user. The custom-fit body engagement member may be produced in any suitable way, such as by a mill, a lathe, a 3D printer, injection molding, or any other suitable means of rapid prototyping or low-volume manufacture. The custom-fit configuration may be obtained in any suitable way, such as through direct or indirect 3D scanning, impression molding, photogrammetry, sample fitting, hand measurement, or combination thereof, of the user.

In some examples, a wearable device may be configured for consistent placement on the user's body based on a custom fit design. For instance, a 3D scan of the exterior topology of the region-of-interest on the user's body may be used to create a custom support assembly. The custom support assembly may be used in conjunction with a custom designed and fabricated wearable device (e.g., helmet). Alternatively, the custom support assembly may be configured to be used with (e.g., connected to or supported by) an off-the-shelf wearable device (e.g., helmet or other wearable component fabricated in predetermined shapes and/or sizes), thereby allowing a customized fit for the user without requiring a costly fully custom fabricated unit. The custom support assembly may be a separate piece permanently affixed to a wearable device. Alternatively, the custom support assembly may be removable or completely integrated into the wearable device during fabrication.

In some examples, the custom support assembly may be optimized through a computerized-algorithm to minimize or increase pressure on the user's body in specific areas by changing a modifiable parameter of the support assembly (e.g., the density, shape, material, spacing, or any other parameter of the support assembly). Additionally or alternatively, the custom support assembly may be optimized for thermal safety and/or comfort, such as increasing airflow or insulation in specific areas.

A 3D scan of the exterior topology of the region-of-interest on the user's body may be obtained in any suitable way. In some examples, one or more kiosks may be provided at point-of-sale locations where users may be scanned by a 3D scanner and receive a 3D print of their custom support assembly. The custom support assembly may also be installed into one of the previously mentioned semi-custom wearable devices (e.g., helmets) while the users wait. Such methods may provide time- and cost-effective means of providing a custom fit wearable device with targeted placement of a wearable assembly or wearable module. In addition, such methods provide significant performance benefits by optimizing the position of wearable assemblies and wearable modules, resulting in an improved experience for the user at a lower overall all-in cost. Additionally, cosmetic and/or aesthetic modifications to a wearable device and/or support assembly design may be incorporated to allow further customization of the wearable device and optical measurement system to suit user tastes and preferences.

Additionally or alternatively to mechanical systems and methods, as position alignment system 1306 may implement sensor-based devices and alignment methods. Sensor-based systems and methods involve the use of a sensor (e.g., a camera, a time-of-flight sensor, etc.) to determine the correct positioning of wearable device 1304 on the user's body. As will be described below in more detail, the sensor may be integrated into wearable device 1304, included in another device worn by the user, or included in a separate device that is not worn by the user. The sensor may be used for an initial fitting and not needed to be performed for subsequent uses, or it may be used for active fitting over time by being implemented for each system use or over a defined or variable usage routine. Cameras may be monoscopic or stereoscopic and may determine the position of the wearable device based on image feature recognition, depth sensing (e.g., time-of-flight), photogrammetric processing, etc. The cameras may image in visible light and/or non-visible light (e.g., infrared).

Figure 15:
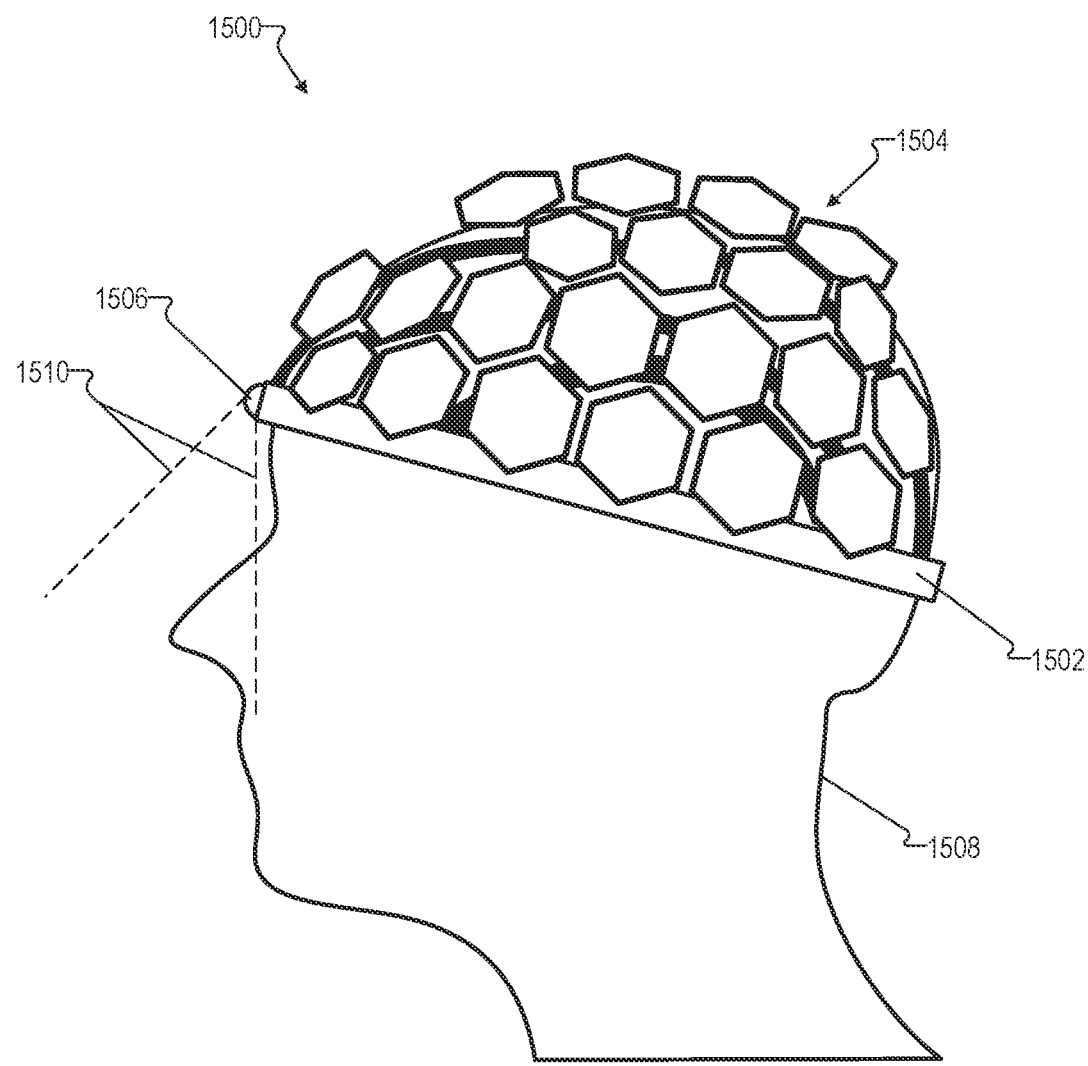
FIG. 15 shows an exemplary wearable device including an integrated sensor.

In an integrated position alignment system, one or more sensors may be integrated with (e.g., included in, supported by, etc.) wearable device 1304 and used to determine a position of wearable device 1304, as shown in FIG. 15. FIG. 15 shows an exemplary wearable device 1500 (e.g., wearable device 1304) including a support assembly 1502, a plurality of wearable module assemblies 1504 (e.g., wearable assemblies 1308), and an integrated sensor 1506 supported by support assembly 1502 (e.g., by a body support portion). Integrated sensor 1506 may be communicatively coupled with a processing unit (not shown) configured to receive and process a detection result of integrated sensor 1506. Integrated sensor 1506 and/or the processing unit may implement position alignment system 1306. The processing unit may be included in wearable device 1500 (e.g., may be supported by support assembly 1502 or included in a wearable module included in a wearable module assembly 1504) or located remotely from wearable device 1500 (e.g., in a remote controller unit).

In some examples, integrated sensor 1506 comprises a camera registered with wearable device 1500 (e.g., registered with support assembly 1502 and/or one or more wearable module assemblies 1504) and configured to image the front of the user's head 1508, as indicated by dashed field-of-view lines 1510. Additionally or alternatively, one or more cameras may be supported by support assembly 1502 above the user's ears and configured to image the user's ears. The camera(s) may be implemented by any suitable imaging device. Position alignment system 1306 may identify, based on the captured image(s) depicting the user's body, anatomical features (e.g., the tip of the nose, ears, moles on the user's skin, eyebrows, eyes, the chin, cheekbones, lips, scars, etc.) and record in memory the reference positions, in the captured image(s), of the anatomical features. The next time the user wears the wearable device 1500, position alignment system 1306 may compare the image(s) captured by the cameras with the previously recorded reference positions to determine if the current position of wearable device 1500 is consistent with the prior recorded reference position.

In additional or alternative examples, integrated sensors 1506 may be configured to determine a distance to a particular anatomical feature. For example, integrated sensor 1506 may be implemented by a time-of-flight sensor, a line scan ranging system, or any other suitable depth sensor configured to measure a distance to the user's nose (or other anatomical feature). Position alignment system 1306 may record the measured distance to the particular anatomical feature. The next time the user wears wearable device 1500, position alignment system 1306 may compare a currently measured distance by the same integrated sensor 1506 with the previously recorded reference measurement to determine if the position of wearable device 1500 is consistent with the prior recorded reference position.

In some examples, one or more integrated sensors 1506 may be configured to generate data representative of a 3D depth map of the user's body (e.g., the user's face, the user's head, etc.). The 3D depth map may be used in any of the ways described above to determine the position of wearable device 1500 relative to head 1508.

In the examples described above, integrated sensor 1506 is configured to determine the position of wearable device 1500 relative to an anatomical feature. In additional or alternative examples, integrated sensor 1506 may be configured to determine the position of wearable device 1500 relative to a non-anatomical feature (not shown), such as another wearable unit (e.g., eyeglasses, a virtual reality (VR) or augmented reality (AR) headset, a hearing aid, an earring, a nose ring, a tattoo, etc.). For example, integrated sensor 1506 may be configured to image (or measure a distance to) a VR/AR headset worn by the user. In some examples, a fiducial marker may be placed on the non-anatomical feature to act as a specific reference point.

In some examples, wearable device 1500 may be configured to determine a position of wearable device 1500 on user's head 1508 based on another wearable device (e.g., a VR/AR headset) that has been registered with the user's head 1508. For example, a VR/AR headset may be registered to the user's head, such as by eye alignment (e.g., eye tracking), photogrammetry, or any other suitable alignment method. A position of wearable device 1500 may then be determined relative to the VR/AR headset and, hence, relative to head 1508. In some examples, wearable device 1500 may include one or more connection members configured to physically connect wearable device 1500 with the VR/AR headset. In this way, the VR/AR headset may be used to positionally align wearable device 1500 with head 1508.

Figure 16:
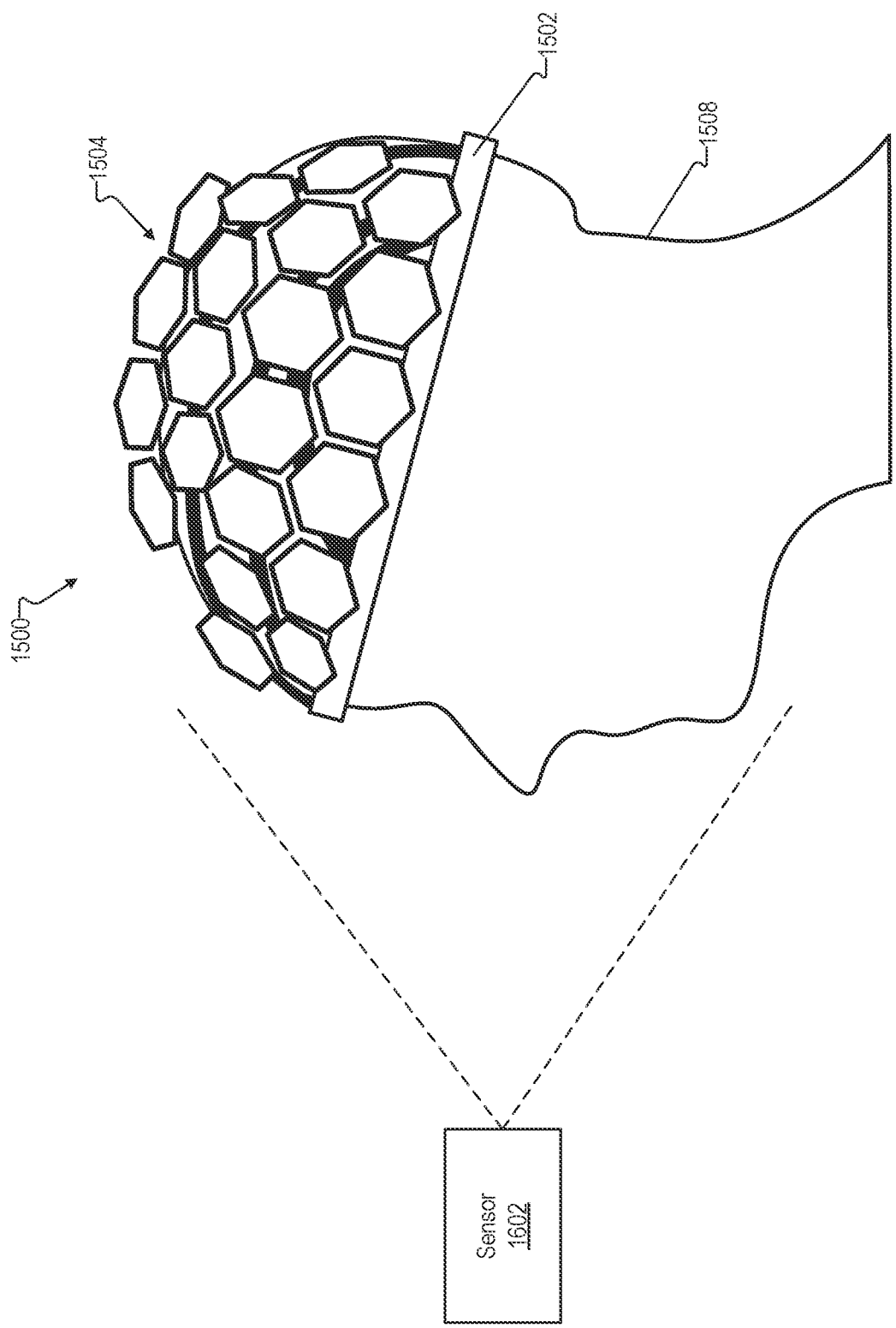
FIG. 16 shows an exemplary wearable device and an external sensor.

Additionally or alternatively to integrated sensors, position alignment system 1306 (see FIGS. 13A and 13B) may use one or more external sensors that are external to (e.g., physically independent of or separated from) wearable device 1304, as shown in FIG. 16. FIG. 16 is similar to FIG. 15 except that in FIG. 16 integrated sensor 1506 is replaced with external sensor 1602. Any of the methods described above that may be performed with integrated sensor 1506 may also be performed with external sensor 1602. For example, external sensor 1602 may be configured to capture one or more images of the user and wearable device 1500, generate a depth map of the user and wearable device 1500, and/or measure a distance to the user or wearable device 1500. To illustrate, external sensor 1602 may comprise a camera configured to capture images depicting the user and wearable device 1500 (including support assembly 1502) on head 1508. Position alignment system 1306 may identify, based on the captured image(s), wearable device 1500 and one or more anatomical features (e.g., the nose). Position alignment system 1306 may then record in memory the position of wearable device 1500 relative to the one or more anatomical features. The next time the user wears the wearable device 1500, position alignment system 1306 may compare image(s) captured by the camera with the previously recorded reference images to determine if the position of wearable device 1500 is consistent with the prior recorded position.

In some examples, position alignment system 1306 may use one or more reference points (e.g., fiducial markers) on wearable device 1500 (e.g., on support assembly 1502, on a wearable assembly, or on a wearable module included in wearable device 1500) and/or one or more anatomical features (e.g., eyes, ears, nose, scars, moles, etc.) or non-anatomical features (e.g., eyeglasses, earrings, nose rings, etc.) to determine a position of the reference point on wearable device 1500 relative to the anatomical or non-anatomical feature. In some embodiments, a fiducial marker may be placed on the user's body (e.g., head or face) independent of wearable device 1500 or any other wearable device or unit (e.g., VR/AR glasses, eyeglasses, etc.) worn by the user. The fiducial marker may be, for example, a retroreflective marker, such as a marker used for 3D imaging of bodies and/or for tracking movements to generate animated images. Such fiducial marker may be attached to a known mark on the user's body (e.g., shoulders, nose, ears, etc.) and one or more additional fiducial markers could be attached to wearable device 1500. In this way, the position of wearable device 1500 relative to the fiducial marker on the user's body can be determined and adjusted to achieve the proper positioning.

In some examples, external sensor 1602 and a processing unit may be included as part of optical measurement system 1302. For example, external sensor 1602 and the processing unit may be included in a remote controller (e.g., controller 112) or computing device (e.g., laptop, processing unit, remote processor 512, etc.). In alternative examples, external sensor 1602 and/or the processing unit may be included in a mobile device (e.g., a smartphone, a tablet, etc.).

Additionally or alternatively to mechanical- and sensor-based position alignment systems and methods, position alignment system 1306 may use signal-based position alignment systems and methods in which position alignment is based on signals detected by wearable assemblies 1308 included in wearable device 1304. For example, the user may be prompted to perform a routine task for which the neural signal is known. Optical measurement system 1302 may measure the neural signals during performance of the task. Position alignment system 1306 may determine, based on the location (e.g., particular detectors or wearable modules in wearable device 1304) of the detected neural signal that matches the known signal, the position of wearable device 1304 relative to the user's head. In additional or alternative examples, a stimulus for which the evoked neural or biological response signal is known may be applied to the user to determine and guide adjustment of the position of wearable device 1304 on the user.

In the examples described above, position alignment system 1306 may determine a position of wearable device 1304 and determine if a current position of wearable device 1304 matches a recorded reference position for wearable device 1304. In some examples, position alignment system 1306 may also be configured to notify (e.g., via a visual, audio, and/or haptic notification) the user when the present position of wearable device 1304 is the same as a previously recorded reference position of wearable device 1304 on the body of the user. Additionally or alternatively, position alignment system 1306 may guide the user to adjust wearable device 1304 to the recorded reference position. For instance, position alignment system 1306 may show presently captured images from integrated sensor 1506 and/or external sensor 1602 and the reference position on a display screen of a connected device (e.g., a computer, a smartphone, a tablet, a remote controller, etc.) so the user can easily determine how to adjust wearable device 1304. Position alignment system 1306 may be configured to guide the user to reposition wearable device 1304 until the present position substantially matches the recorded reference position.

Wearable device 1304 may be adjusted in any of the ways described herein. For example, wearable device 1304 may be adjusted manually. Additionally or alternatively, position alignment system 1306 may automatically adjust wearable device 1304 by driving, based on the present position and the reference position, one or more mechanical actuators or motors to adjust a position of wearable device 1304 (e.g., a position of body support portion 804, a position of support members 806, and/or a position of a wearable assembly, wearable module assembly, and/or wearable module supported by support members 806). In some embodiments, position alignment system 1306 may enable consistent positioning of wearable device 1304 during multiple different use sessions with no more than one (1) centimeter (cm) of variability.

In the embodiments described above, position alignment system 1306 may determine the position of wearable device 1304 as a whole relative to the user's body (e.g., the user's head). Additionally or alternatively, position alignment system 1306 may determine the position of each individual wearable assembly, wearable module assembly, and/or wearable module relative to the user's body in any of the ways described above for positioning of wearable device 1304. In some examples, position alignment system 1306 may determine that only one wearable assembly 1308 (e.g., wearable module assembly 1006-2, see FIG. 10) in wearable device 1304 is out of alignment and thus guide the user to reposition that wearable assembly 1308.

Position alignment system 1306 may also be used to perform coarse adjustments prior to use of wearable device 1304 by the user. For instance, measurements (size, location, etc.) of the user's body (e.g., head) may be input as fitting data to position alignment system 1306. Position alignment system 1306 may model, based on the fitting data, the shape of the user's body and determine the appropriate size and position settings for the wearable device, support assembly (e.g., body support portion and support members), and wearable assemblies. In this way, the wearable device can be coarsely adjusted prior to use by the user to speed up the positioning procedure.

In some examples, a 3D model of the target (e.g., user's brain), such as an MRI scan, a CT scan, an EEG scan, a transcranial doppler ultrasound scan, a conventional ultrasound scan, and the like, may be input as model data to position alignment system 1306. Position alignment system 1306 may use the model data to identify the locations of the target and specific regions-of-interest and identify proper positions of wearable device 1304 (e.g., a position of wearable device 1304 on the user's body, a position of support members in wearable device 1304, and/or a position of one or more wearable assemblies 1308 supported by the support members) to image the target at the region-of-interest.

The preceding description describes using various wearable device positioning systems and method to aid adjustment of the position of a wearable device, wearable assemblies, wearable module assemblies, and/or wearable modules on the user's body. In other embodiments, it may be possible to use wearable device position information to calibrate the wearable module detection results without requiring the user to reposition the wearable device. By knowing the position of the wearable device relative to the user's body, an optical measurement system or position alignment system can correct the acquired data to correspond to data acquired from a recorded reference position. For example, wearable modules 1008 (see FIGS. 10 and 11) may be calibrated to identify where they are relative to each other. This may be done in any suitable way, such as is described in the co-pending Provisional Patent Application No. 63/071,473, filed on Aug. 28, 2020, entitled "Estimation of Source-detector Separation in an Optical Measurement System," incorporated herein in its entirety. In such system, the observation of a plurality of known neural signal sources (e.g., three) having known positions relative to one other and to the entire signal area of interest may be used to infer the position to the surrounding morphology (particularly if the detected neural signals are consistent enough over time, e.g., have no neural plasticity or the like which would alter the response to a known calibration stimulus).

Figure 17A:
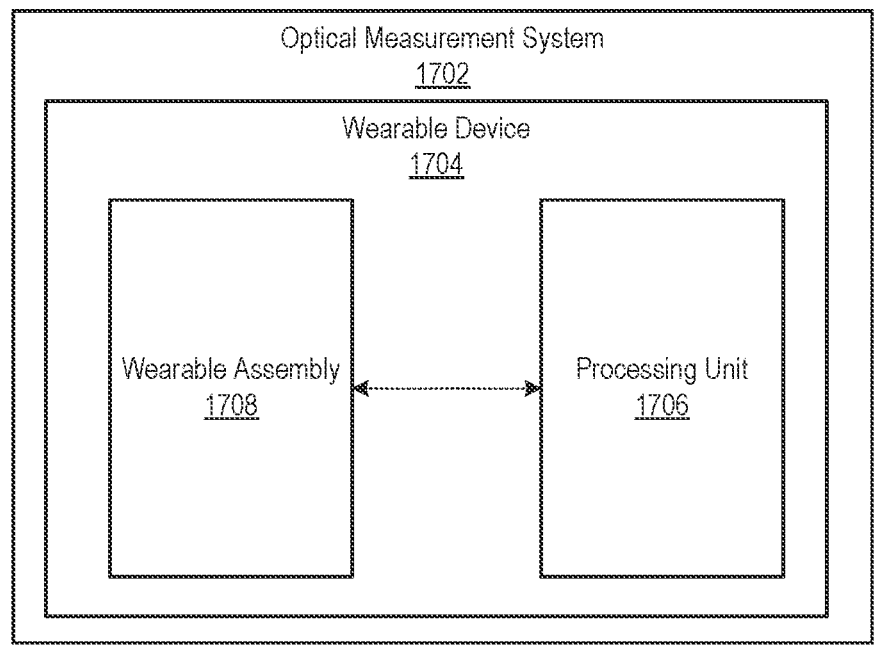
FIGS. 17A and 17B illustrate exemplary configurations of an exemplary optical measurement system that includes a processing unit.
Figure 17B:
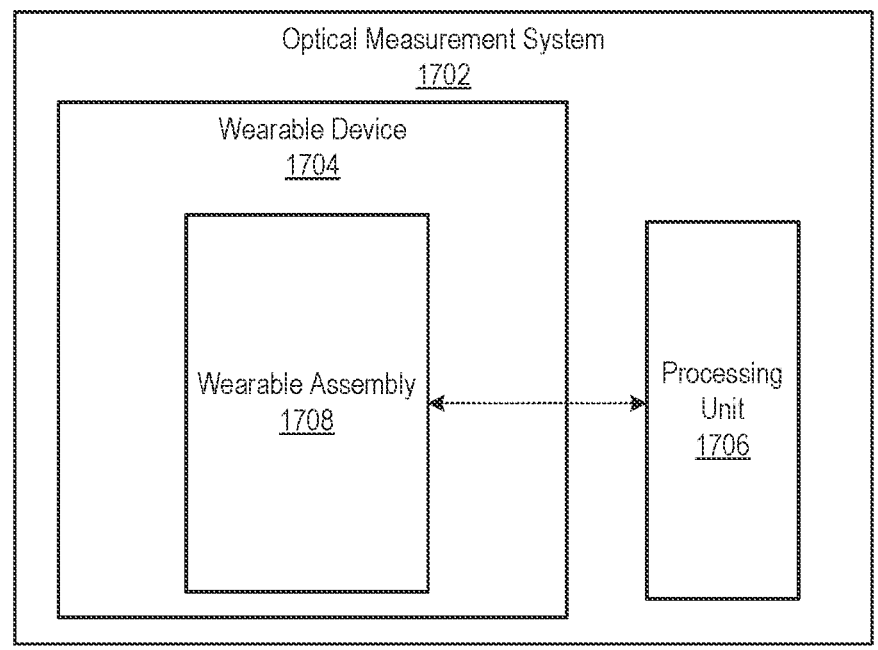

In some examples, optical measurement systems described herein (e.g., optical measurement system 100 or optical measurement system 1302) may include a processing unit configured to perform one or more operations based on photon arrival times detected by the detectors described herein, and perform one or more position alignment operations. For example, FIGS. 17A-17B show illustrative configurations 1700-1 and 1700-2 of an exemplary optical measurement system 1702 in accordance with the principles described herein.

Optical measurement system 1702 may be an implementation of optical measurement system 100 or optical measurement system 1302 and, as shown, includes a wearable device 1704 and a processing unit 1706. Wearable device 1704 may be implemented by any wearable device described herein and may include a wearable assembly 1708. Processing unit 1706 may perform any operations described herein. In some examples, processing unit 1706 implements position alignment system 1306. Wearable assembly 1708 may be implemented by any wearable assembly described herein. In some examples, optical measurement system 1702 may include a plurality of wearable assemblies 1708. Optical measurement system 1702 may also include any other components as may serve a particular implementation.

In configuration 1700-1, processing unit 1706 is included in wearable device 1704 (e.g., supported by support assembly 802, included wearable assembly 1708, included in a housing of a wearable module 702, etc.). In configuration 1700-2, processing unit 1706 is not included in wearable device 1704 (i.e., processing unit 1706 is housed in an additional housing of a device located external to wearable device 1704). Either configuration 1700-1 or 1700-2 may be used in accordance with the systems, circuits, and methods described herein.

Detectors on wearable assembly 1708 may output signals representative of photon arrivals, as described herein. Processing unit 1706 is configured to receive the output signals and perform one or more operations based on the signals. For example, processing unit 1706 may generate measurement data (e.g., one or more histograms) based on the signals, as described herein.

As mentioned, in configuration 1700-2, processing unit 1706 is not included in wearable device 1704. For example, processing unit 1706 may be included in a wearable device separate from wearable device 1704. To illustrate, processing unit 1706 may be included in a wearable device configured to be worn off the head (e.g., on a belt) while wearable device 1704 is worn on the head. In these examples, one or more communication interfaces (e.g., cables, wireless interfaces, etc.) may be used to facilitate communication between wearable device 1704 and the separate wearable device.

Additionally or alternatively, in configuration 1700-2, processing unit 1706 may be remote from the user (i.e., not worn by the user). For example, processing unit 1706 may be implemented by a stand-alone computing device communicatively coupled to wearable device 1704 by way of one or more communication interfaces (e.g., cables, wireless interfaces, etc.).

In some examples, processing unit 1706 may be distributed between multiple devices and/or multiple locations as may serve a particular implementation. Processing unit 1706 may be implemented by processor 108, controller 112, control circuit 244, and/or any other suitable processing and/or computing device or circuit.

Figure 18:
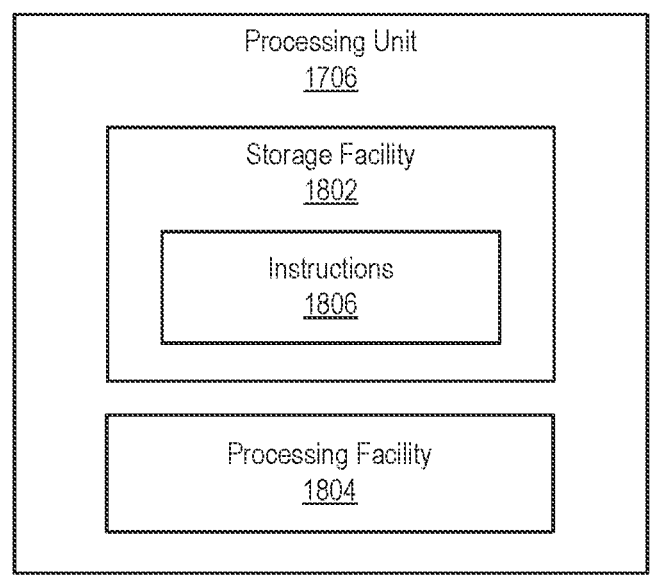
FIG. 18 illustrates an exemplary implementation of the processing unit of FIGS. 17A and 17B.

For example, FIG. 18 illustrates an exemplary implementation of processing unit 1706 in which processing unit 1706 includes a memory (storage facility) 1802 and a processor (processing facility) 1804 configured to be selectively and communicatively coupled to one another. In some examples, memory 1802 and processor 1804 may be distributed between multiple devices and/or multiple locations as may serve a particular implementation.

Memory 1802 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1802 may maintain (e.g., store) executable data used by processor 1804 to perform one or more of the operations described herein. For example, memory 1802 may store instructions 1806 that may be executed by processor 1804 to perform any of the operations described herein. Instructions 1806 may be implemented by any suitable application, program (e.g., sound processing program), software, code, and/or other executable data instance. Memory 1802 may also maintain any data received, generated, managed, used, and/or transmitted by processor 1804.

Processor 1804 may be configured to perform (e.g., execute instructions 1806 stored in memory 1802 to perform) various operations described herein. For example, processor 1804 may be configured to perform any of the operations described herein as being performed by processing unit 1706.

FIGS. 19-24 illustrate embodiments of a wearable device 1900 that includes elements of the optical measurement systems and/or wearable assemblies described herein. In particular, the wearable devices 1900 include a plurality of modules 1902, similar to modules 702 described herein. For example, each module 1902 includes a light source 704 and a plurality of detectors 706. Light source 704 may be implemented by or be similar to one or more light sources described herein (e.g., light source 110). Each detector 706 may implement or be similar to one or more detectors or detector assemblies described herein (e.g., detector 104) and may include a plurality of photodetectors. The wearable devices 1900 may each also include a controller (e.g., controller 112) and a processor (e.g., processor 108) and/or be communicatively connected to a controller and/or a processor. In general, wearable device 1900 may be implemented by any suitable headgear and/or clothing article configured to be worn by a user. The headgear and/or clothing article may include batteries, cables, and/or other peripherals for the components of the optical measurement systems described herein. In some examples, the headgear includes one or more modules 1902. Additionally or alternatively, modules 1902 are included in or implemented by modules 702.

Figure 19:
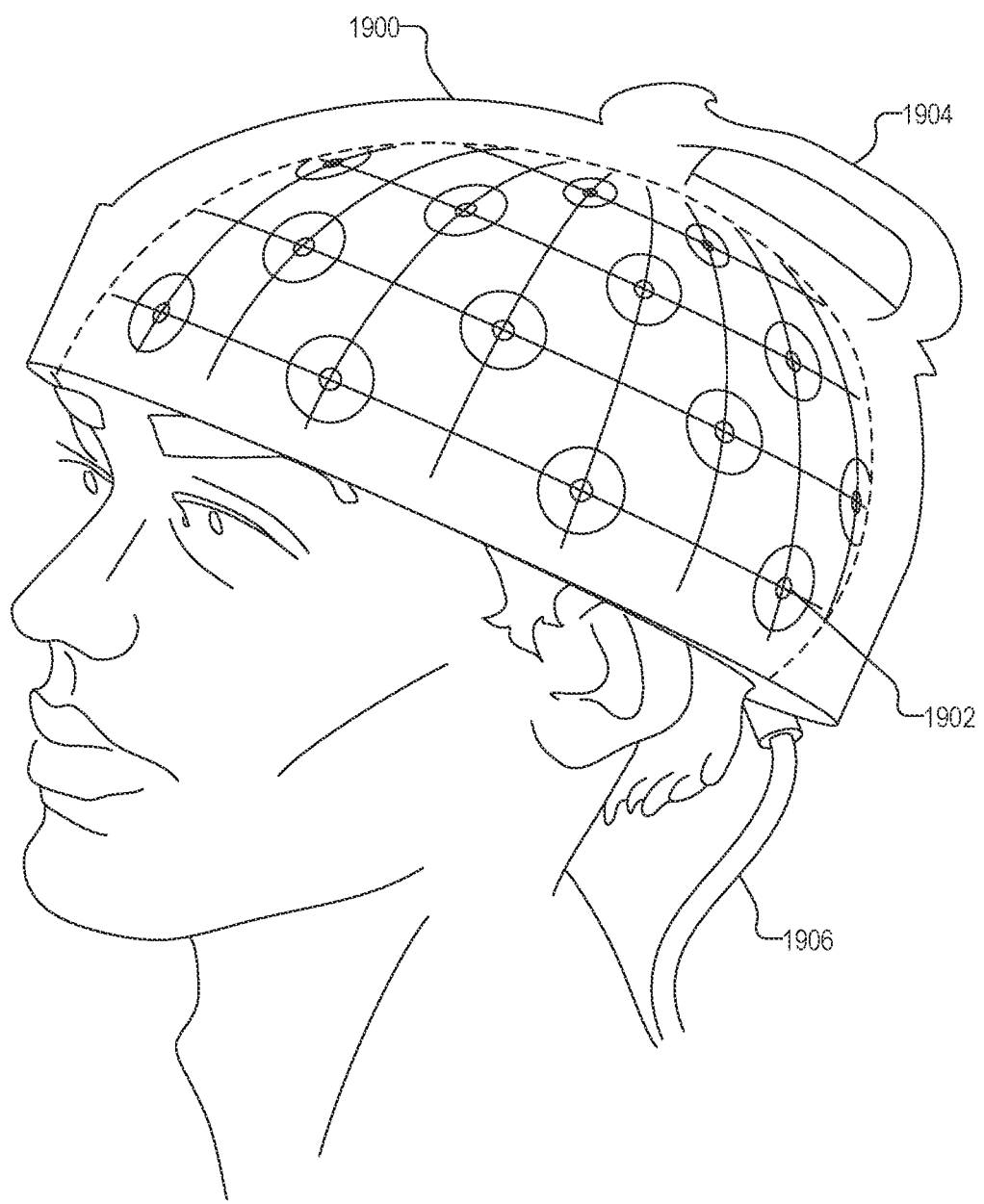
FIGS. 19-24 illustrate exemplary embodiments of a wearable device that includes elements of the optical measurement systems described herein.
Figure 20:
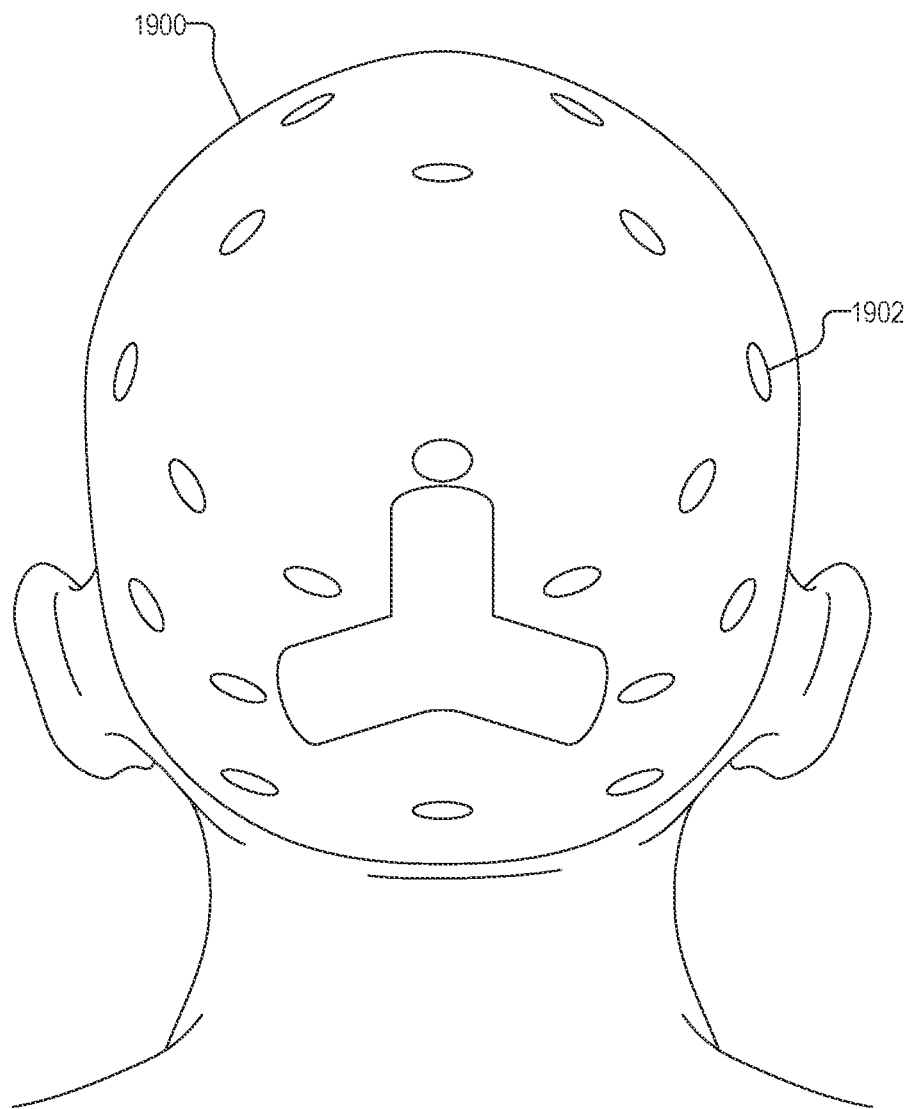
Figure 21:
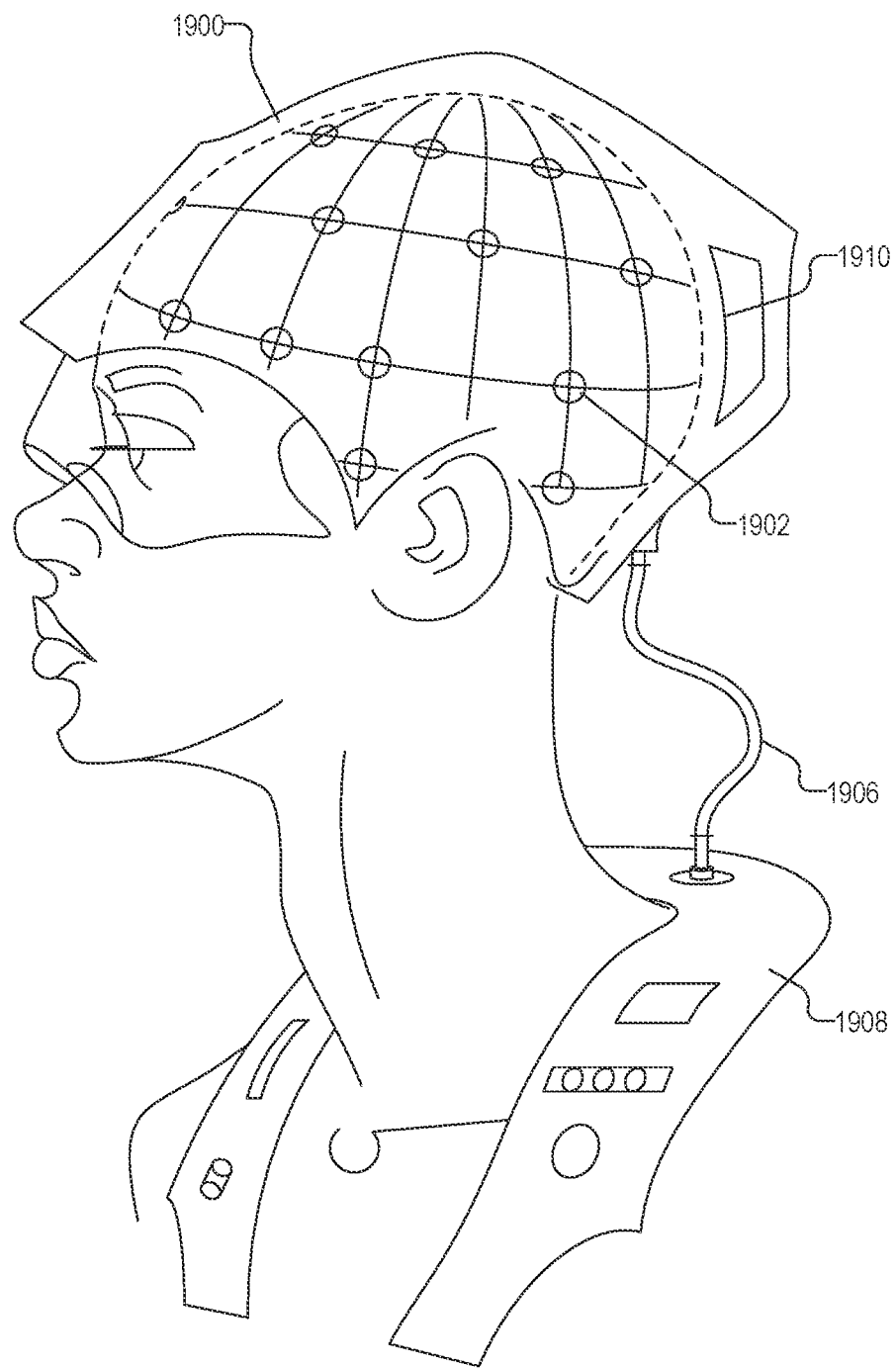

FIG. 19 illustrates an embodiment of a wearable device 1900 in the form of a helmet with a handle 1904. A cable 1906 extends from the wearable device 1900 for attachment to a battery or hub (with components such as a processor or the like). FIG. 20 illustrates another embodiment of a wearable device 1900 in the form of a helmet showing a back view. FIG. 21 illustrates a third embodiment of a wearable device 1900 in the form of a helmet with the cable 1906 leading to a wearable garment 1908 (such as a vest or partial vest) that can include a battery or a hub (e.g., processing unit 1706). Alternatively or additionally, the wearable device 1900 can include a crest 1910 or other protrusion for placement of the hub or battery.

Figure 22:
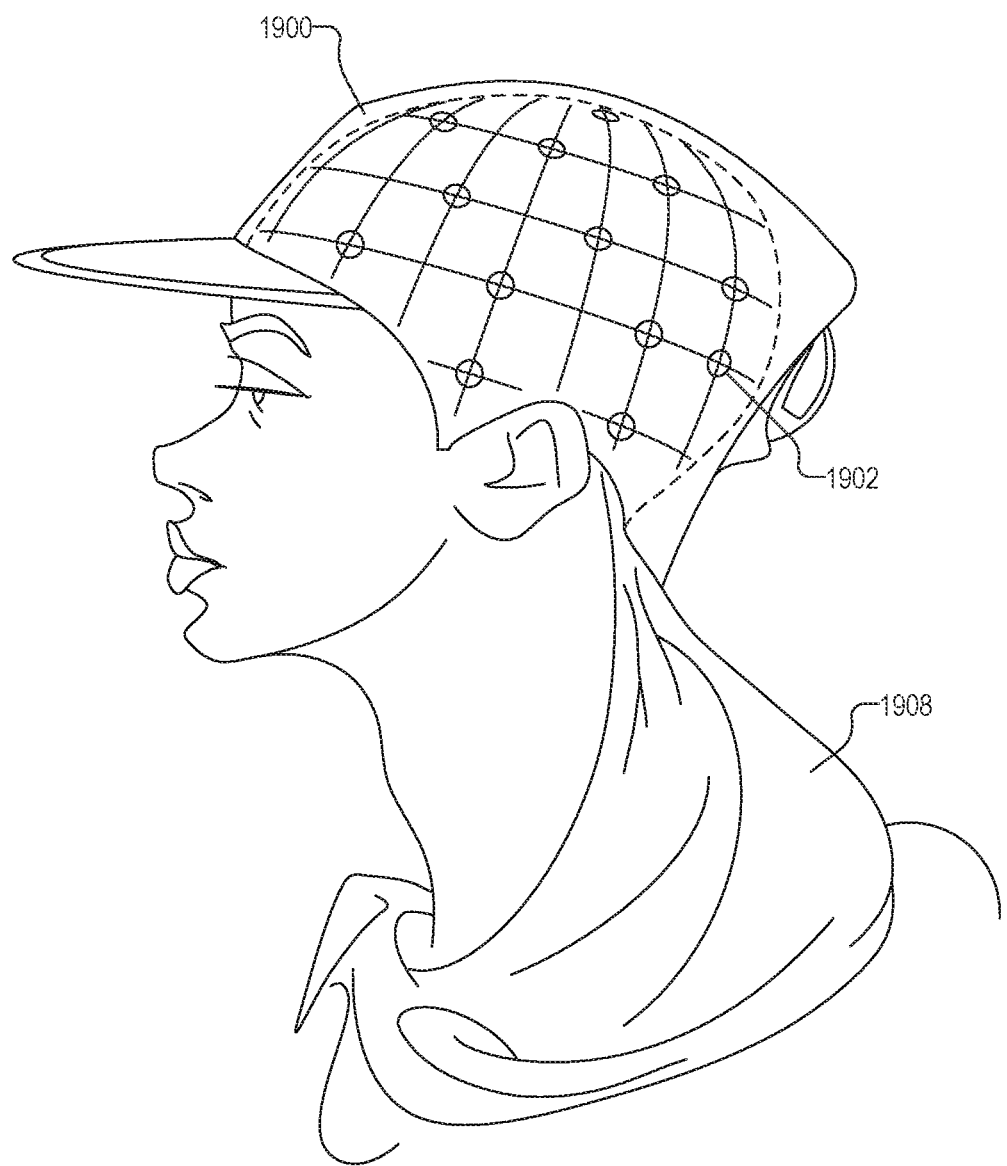
Figure 23:
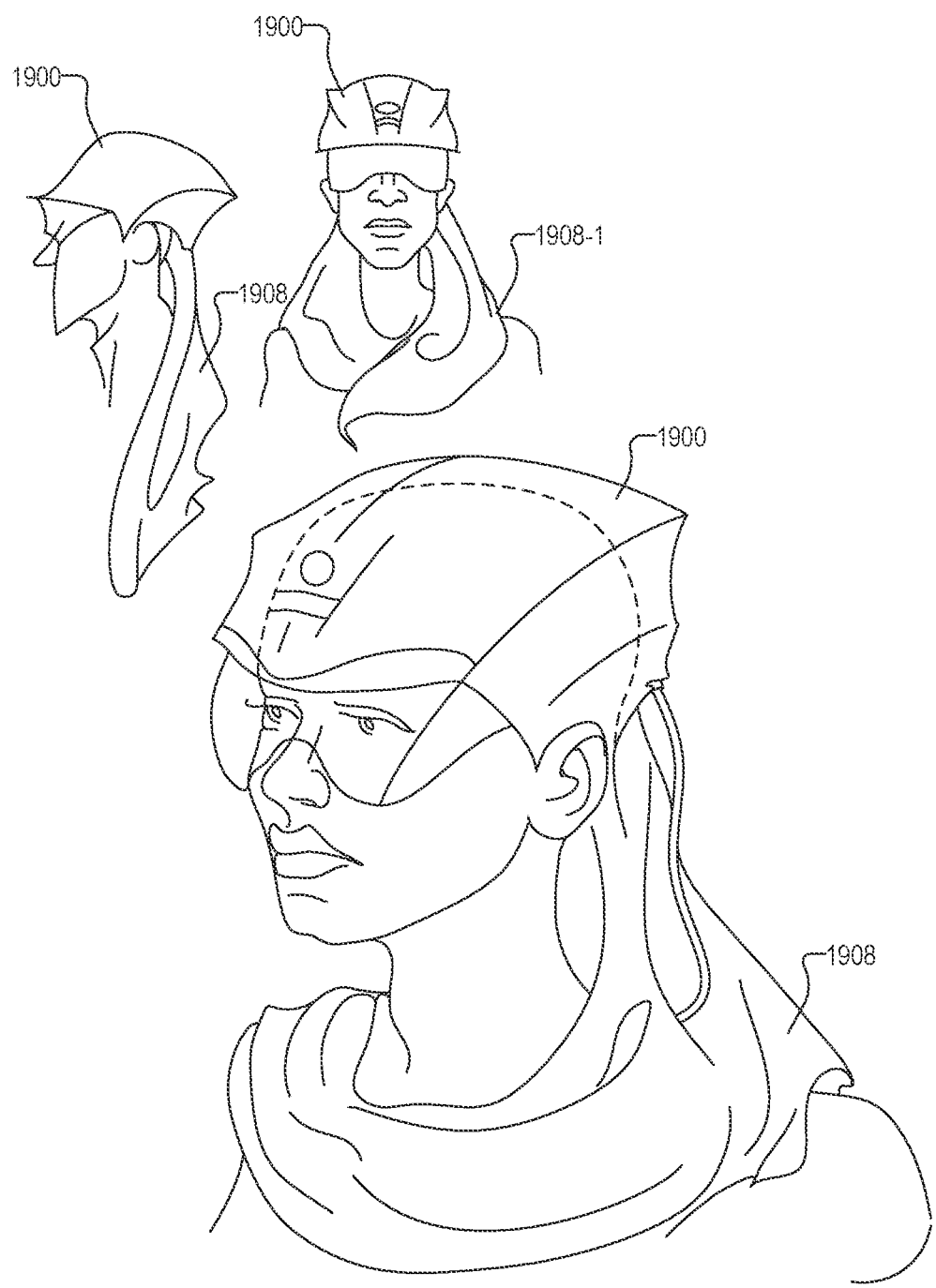
Figure 24:
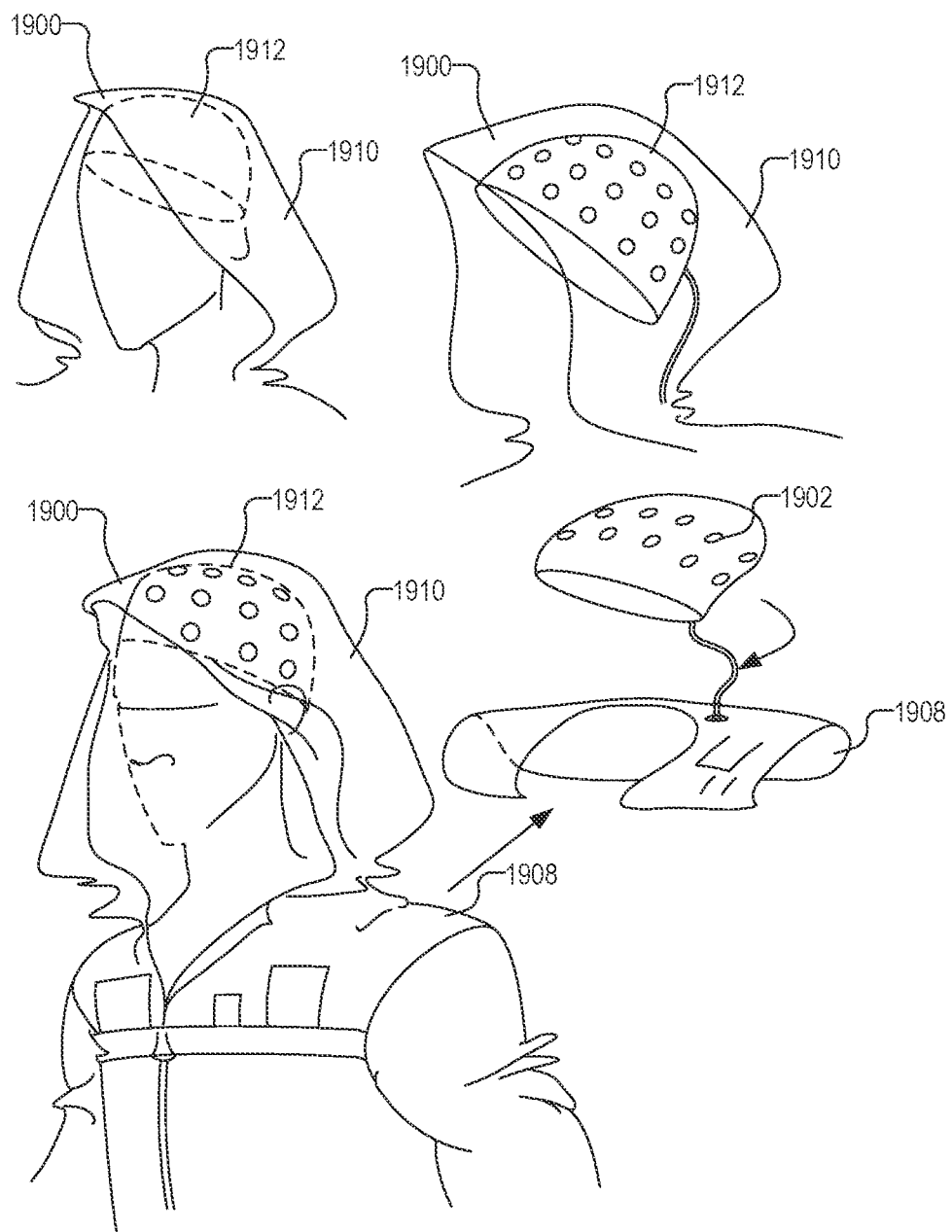

FIG. 22 illustrates another embodiment of a wearable device 1900 in the form of a cap with a wearable garment 1908 in the form of a scarf that may contain or conceal a cable, battery, and/or hub. FIG. 23 illustrates additional embodiments of a wearable device 1900 in the form of a helmet with a one-piece scarf 1908 or two-piece scarf 1908-1. FIG. 24 illustrates an embodiment of a wearable device 1900 that includes a hood 1910 and a beanie 1912 which contains the modules 1902, as well as a wearable garment 1908 that may contain a battery or hub.

In some examples, a wearable device (e.g., wearable device 800 or 1900) may include a pressing member configured to press, to a conformable fitting position as may serve a particular use session, the plurality of wearable modules toward the surface of the body of the user when the wearable module assembly is worn on the body of the user. Thus, the pressing member may help maintain contact of the light sources (e.g., light sources 704) and detectors (e.g., detector 706) with the body surface. The pressing member may include, for example, an elastic band, a strap, a hat, an inflatable bag within a helmet, or any other suitable device configured to press the wearable assembly against the body surface. For instance, the helmets shown in FIGS. 19 and 20 may cover wearable module assembly 700 and be configured to press modules 702 against the user's head. In some examples, the fit of the helmets is adjustable to produce the pressing force, as may be required, in order to support the helmet on the desired region-of-interest on the user's head. Alternatively, the helmets may include an inflatable airbag that presses wearable module assembly 700 against the user's head.

Figure 25:
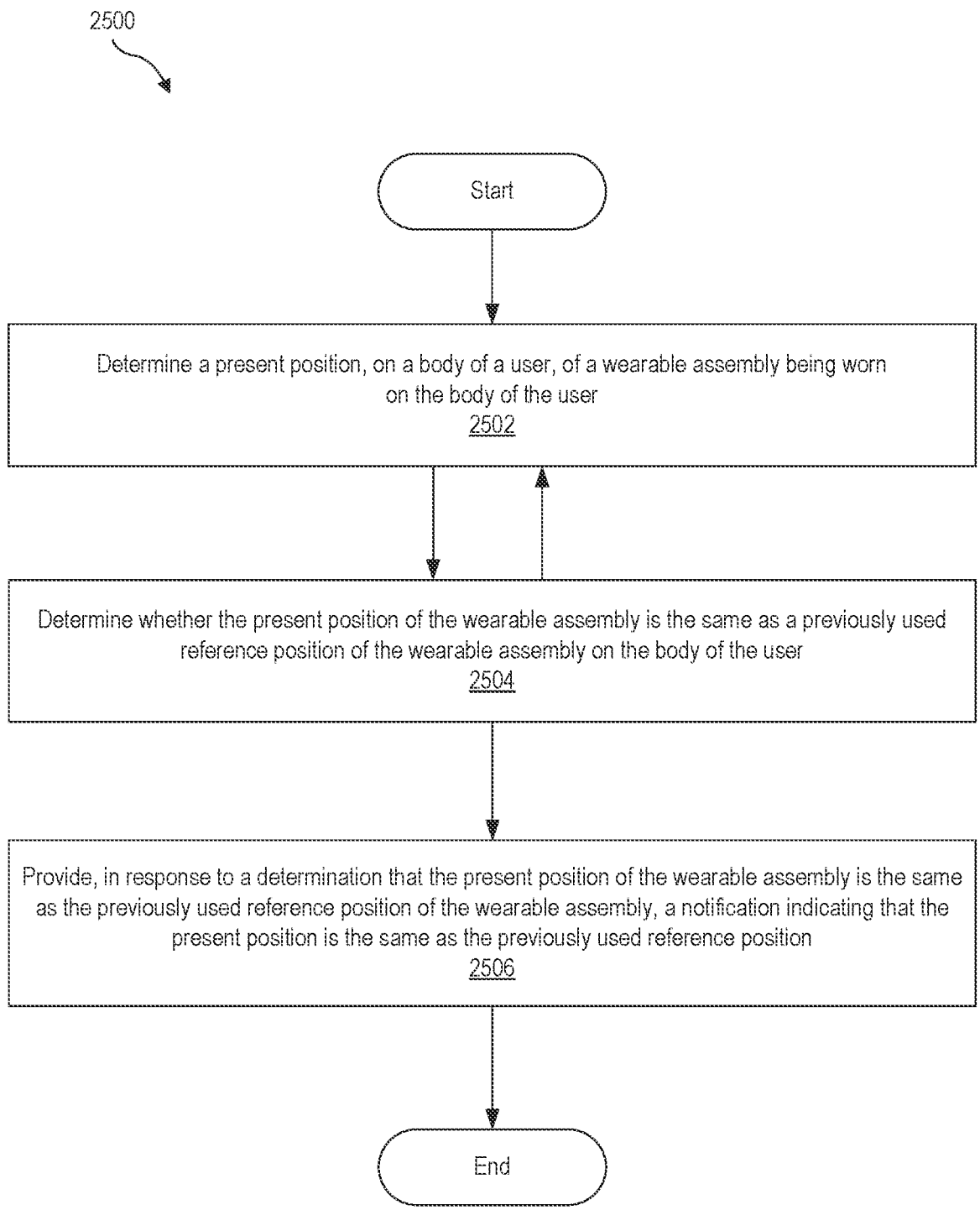
FIG. 25 illustrates an exemplary method.

FIG. 25 illustrates an exemplary method 2500. While FIG. 25 illustrates exemplary operations according to one embodiment, other embodiments may omit, add to, reorder, and/or modify any of the operations shown in FIG. 25. One or more of the operations shown in FIG. 25 may be performed by optical measurement system 100, 1302, or 1702, or position alignment system 1306, or any components included therein, and/or any implementation thereof.

In operation 2502, a present position, on a body of a user, of a wearable assembly being worn on the body of the user is determined. Operation 2502 may be performed in any of the ways described herein.

In operation 2504, it is determined whether the present position of the wearable assembly is the same (within a predetermined tolerance, e.g., 1 cm) as a previously used reference position of the wearable assembly on the body of the user. Operation 2504 may be performed in any of the ways described herein.

Operations 2502 and 2504 may be repeated, as needed, until it is determined that the present position of the wearable assembly is the same as the previously used reference position of the wearable assembly on the body of the user. For example, if the present position is determined to not be the same as the previously used reference position, the method returns to operation 2502. If the present position is determined to be the same as the previously used reference position, the method proceeds to operation 2506.

In operation 2506, a notification is provided in response to a determination that the present position of the wearable assembly is the same as the previously used reference position of the wearable assembly. The notification may indicate that the present position of the wearable assembly is the same as the previously used reference position of the wearable assembly. Operation 2506 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 26:
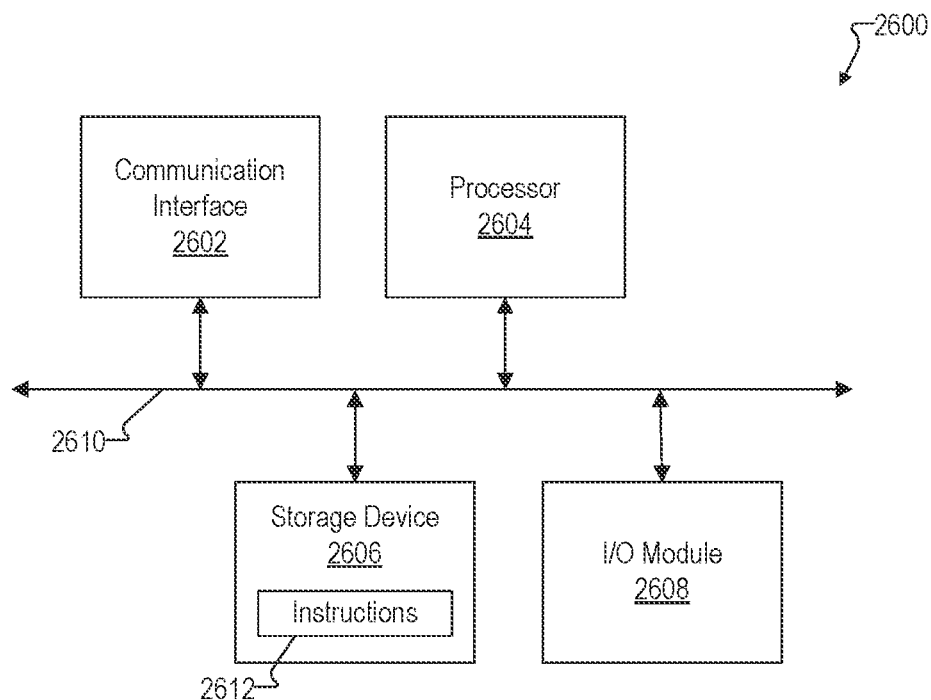
FIG. 26 illustrates an exemplary computing device.

FIG. 26 illustrates an exemplary computing device 2600 that may be specifically configured to perform one or more of the processes described herein. Any of the systems, units, computing devices, and/or other components described herein may be implemented by computing device 2600.

As shown in FIG. 26, computing device 2600 may include a communication interface 2602, a processor 2604, a storage device 2606, and an input/output ("I/O") module 2608 communicatively connected one to another via a communication infrastructure 2610. While an exemplary computing device 2600 is shown in FIG. 26, the components illustrated in FIG. 26 are not intended to be limiting. Additional or alternative components may be used in other embodiments. Components of computing device 2600 shown in FIG. 26 will now be described in additional detail.

Communication interface 2602 may be configured to communicate with one or more computing devices. Examples of communication interface 2602 include, without limitation, a wired network interface (such as a network interface card), a wireless network interface (such as a wireless network interface card), a modem, an audio/video connection, and any other suitable interface.

Processor 2604 generally represents any type or form of processing unit capable of processing data and/or interpreting, executing, and/or directing execution of one or more of the instructions, processes, and/or operations described herein. Processor 2604 may perform operations by executing computer-executable instructions 2612 (e.g., an application, software, code, and/or other executable data instance) stored in storage device 2606.

Storage device 2606 may include one or more data storage media, devices, or configurations and may employ any type, form, and combination of data storage media and/or device. For example, storage device 2606 may include, but is not limited to, any combination of the non-volatile media and/or volatile media described herein. Electronic data, including data described herein, may be temporarily and/or permanently stored in storage device 2606. For example, data representative of computer-executable instructions 2612 configured to direct processor 2604 to perform any of the operations described herein may be stored within storage device 2606. In some examples, data may be arranged in one or more databases residing within storage device 2606.

I/O module 2608 may include one or more VO modules configured to receive user input and provide user output. I/O module 2608 may include any hardware, firmware, software, or combination thereof supportive of input and output capabilities. For example, I/O module 2608 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2608 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2608 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
   a wearable device configured to be worn on a body of a user, comprising:
     a support assembly; and
     a wearable assembly supported by the support assembly and comprising:
       a plurality of light sources configured to emit a plurality of light pulses toward a target within the body of the user; and
       a plurality of detectors each configured to receive a set of photons included in a light pulse included in the plurality of light pulses after the set of photons is scattered by the target; and
   a position alignment system configured to facilitate positioning of the wearable assembly at a same position on the body of the user during different use sessions of the wearable device.

2. The optical measurement system of claim 1, wherein the position alignment system comprises a body engagement member supported by the support assembly and configured to engage with an anatomical feature on the body of the user.

3. The optical measurement system of claim 1, wherein:
   the position alignment system comprises an imaging device configured to capture an image of the body of the user; and
   the position alignment system is configured to determine, based on the image of the body of the user, a present position of the wearable assembly on the body of the user.

4. The optical measurement system of claim 3, wherein the imaging device is included in the wearable device.

5. The optical measurement system of claim 3, wherein the imaging device is separate from the wearable device and the image of the body the user depicts the support assembly worn on the body of the user.

6. The optical measurement system of claim 1, wherein the position alignment system is configured to:
   acquire, from an additional wearable device worn by the user, information indicating a position of the additional wearable device on the body of the user; and
   determine, based on the position of the additional wearable device on the body of the user, a present position of the wearable assembly on the body of the user.

7. The optical measurement system of claim 1, wherein the position alignment system is configured to determine, based on depth data representative of a depth map of the body of the user and the support assembly worn on the body of the user, a present position of the wearable assembly on the body of the user.

8. The optical measurement system of claim 1, wherein the position alignment system is configured to determine, based on a detection result of the plurality of detectors while the support assembly is worn on the body of the user, a present position of the wearable assembly on the body of the user.

9. The optical measurement system of claim 1, wherein:
   the different use sessions comprise a first use session and a second use session that is separate from and subsequent to the first use session; and
   the position alignment system is further configured to guide, during the second use session, the user to adjust the position of the wearable assembly so that the wearable assembly is located at the same position on the body of the user during the second use session as during the first use session.

10. The optical measurement system of claim 1, wherein:
    the position of the wearable assembly on the support assembly is adjustable; and
    the wearable assembly is configured to be positioned at the same position on the body of the user by adjusting the position of the wearable assembly on the support assembly.

11. The optical measurement system of claim 1, wherein:
    the support assembly comprises a support member;
    the wearable assembly is supported by the support member; and
    one or more of a position, a length, or a tension of the support member is adjustable.

12. The optical measurement system of claim 1, further comprising an additional wearable assembly supported by the support assembly,
wherein the support assembly comprises an adjustable connector that connects the wearable assembly with the additional wearable assembly.

13. The optical measurement system of claim 1, wherein:
the support assembly comprises a plurality of support members; and
a tension of the plurality of support members is adjustable.

14. The optical measurement system of claim 1, wherein the support assembly includes a locking member configured to lock the wearable assembly at the position on the support assembly.

15. A method comprising:
determining, by a position alignment system, a present position, on a body of a user, of a wearable assembly being worn on the body of the user, the wearable assembly comprising:
a plurality of light sources configured to emit a plurality of light pulses toward a target within the body of the user; and
a plurality of detectors each configured to receive a set of photons included in a light pulse included in the plurality of light pulses after the set of photons is scattered by the target; and
providing, by the position alignment system, a notification indicating that the present position of the wearable assembly is the same as a previously used reference position of the wearable assembly on the body of the user.

16. The method of claim 15, further comprising:
guiding, by the position alignment system, the user to adjust the position of the wearable assembly so that the present position of the wearable assembly is the same as the previously used reference position of the wearable assembly on the body of the user.

17. The method of claim 15, wherein the determining of the present position of the wearable assembly on the body of the user comprises:
acquiring, by the position alignment system, image data representative of an image of the body of the user captured by an imaging device;
identifying, by the position alignment system based on the image data, an anatomical feature on the body of the user and depicted in the image of the body of the user; and
determining, by the position alignment system based on the image data, the position of the wearable assembly on the body of the user relative to the anatomical feature on the body of the user.

18. The method of claim 17, wherein the imaging device is registered with the wearable assembly.

19. The method of claim 15, wherein the determining of the present position of the wearable assembly on the body of the user is based on a depth map of the body of the user and the wearable assembly.

20. The method of claim 15, wherein the determining of the present position of the wearable assembly on the body of the user comprises:
acquiring, by the position alignment system based on a detection result of the plurality of detectors, a neural signal based on performance of a task by the user;
comparing, by the position alignment system, the acquired neural signal with a known neural signal for performance of the task; and
determining, by the position alignment system based on the comparing of the acquired neural signal with the known neural signal, the present position of the wearable assembly on the body of the user.

* * * * *